US009382232B2

(12) United States Patent
Gong et al.

(10) Patent No.: US 9,382,232 B2
(45) Date of Patent: Jul. 5, 2016

(54) QUINOLINE AND CINNOLINE DERIVATIVES AND THEIR APPLICATIONS

(71) Applicants: Shenyang Pharmaceutical University, Shenyang (CN); Shenyang Pharmaceutical University (Benxi) Pharmaceutical Science and Technology Co., Ltd., Benxi (CN)

(72) Inventors: Ping Gong, Shenyang (CN); Yanfang Zhao, Shenyang (CN); Yajing Liu, Shenyang (CN); Xin Zhai, Shenyang (CN); Sai Li, Shenyang (CN); Wufu Zhu, Shenyang (CN); Mingze Qin, Shenyang (CN)

(73) Assignees: Shenyang Pharmaceutical University, Shenyang (CN); Shenyang Pharmaceutical University (Benxi) Pharmaceutical Science and Technology Co., Ltd., Benxi (CN)

( * ) Notice: Subject to any disclaimer, the term of this patent is extended or adjusted under 35 U.S.C. 154(b) by 0 days.

(21) Appl. No.: 14/369,559

(22) PCT Filed: Dec. 7, 2012

(86) PCT No.: PCT/CN2012/001640
§ 371 (c)(1),
(2) Date: Jun. 27, 2014

(87) PCT Pub. No.: WO2013/097280
PCT Pub. Date: Jul. 4, 2013

(65) Prior Publication Data
US 2014/0364431 A1  Dec. 11, 2014

(30) Foreign Application Priority Data

Dec. 30, 2011 (CN) .......................... 2011 1 0453555
Apr. 17, 2012 (CN) .......................... 2012 1 0111920

(51) Int. Cl.
| | |
|---|---|
| *C07D 403/14* | (2006.01) |
| *C07D 401/12* | (2006.01) |
| *C07D 403/12* | (2006.01) |
| *A61P 35/00* | (2006.01) |
| *A61K 31/496* | (2006.01) |
| *A61K 31/502* | (2006.01) |
| *A61K 31/506* | (2006.01) |

(Continued)

(52) U.S. Cl.
CPC ............ *C07D 403/14* (2013.01); *A61K 31/496* (2013.01); *A61K 31/502* (2013.01); *A61K 31/506* (2013.01); *A61K 31/5377* (2013.01); *C07D 401/12* (2013.01); *C07D 401/14* (2013.01); *C07D 403/12* (2013.01)

(58) Field of Classification Search
CPC .. C07D 401/12; C07D 401/14; C07D 403/12; C07D 403/14; A61K 31/496; A61K 31/502; A61K 31/506; A61K 31/5377
See application file for complete search history.

(56) References Cited

U.S. PATENT DOCUMENTS

| | | | | |
|---|---|---|---|---|
| 7,425,564 | B2 * | 9/2008 | Fujiwara ................ | A61K 31/47 514/312 |
| 9,120,778 | B2 * | 9/2015 | Dandu ................ | C07D 401/12 |
| 2004/0166544 | A1 | 8/2004 | Morton et al. | |

(Continued)

FOREIGN PATENT DOCUMENTS

| | | | | |
|---|---|---|---|---|
| CN | 101553232 A | | 8/2010 | |
| CN | 102643268 A | * | 8/2012 | ........... C07D 403/12 |

(Continued)

OTHER PUBLICATIONS

Gong et al. "Quinoline and cinnoline compound and application thereof" CN102643268A (Aug. 22, 2012) English Machine translation.*

(Continued)

*Primary Examiner* — Nyeemah A Grazier
*Assistant Examiner* — Amanda L Aguirre
(74) *Attorney, Agent, or Firm* — Kilpatrick Townsend & Stockton LLP

(57) ABSTRACT

The present invention relates to a series of quinoline and cinnoline derivatives of general formula I, pharmaceutically acceptable salts, hydrates, solvates or prodrugs thereof. And the compounds of general formula I show potent inhibitory activity gainst c-Met kinase. The present invention further relates to the uses of the compounds, pharmaceutically acceptable salts and hydrates for the preparation of medicaments for the treatment and/or prevention of diseases caused by abnormal expression of c-Met kinase, especially for treatment and/or prevention of cancer.

(I)

17 Claims, No Drawings

(51) Int. Cl.
*A61K 31/5377* (2006.01)
*C07D 401/14* (2006.01)

(56) References Cited

U.S. PATENT DOCUMENTS

| | | | |
|---|---|---|---|
| 2005/0037431 A1 | 2/2005 | Kirchhofer et al. | |
| 2008/0207617 A1* | 8/2008 | Miwa | A61K 31/47 514/235.2 |
| 2012/0219522 A1* | 8/2012 | Xi | C07D 401/12 424/85.4 |
| 2014/0371221 A1* | 12/2014 | Xu | C07D 401/14 514/235.2 |
| 2015/0307453 A1* | 10/2015 | Gong | C07D 401/12 514/235.2 |

FOREIGN PATENT DOCUMENTS

| | | | |
|---|---|---|---|
| EP | 1411046 A1 * | 4/2004 | |
| GB | WO97/04775 A1 * | 2/1997 | |
| JP | WO2005/094805 A1 * | 10/2005 | |
| JP | WO2012/011548 A1 * | 1/2012 | |
| WO | WO03/018579 A1 * | 3/2003 | |
| WO | 2004/006846 A2 | 1/2004 | |
| WO | WO2004/006846 A2 * | 1/2004 | |
| WO | 2005/030140 A2 | 4/2005 | |
| WO | WO2005/030140 A2 * | 4/2005 | |
| WO | 2007/146824 A2 | 12/2007 | |
| WO | WO2007/146824 A2 * | 12/2007 | |
| WO | WO2009/036412 A1 * | 3/2009 | |
| WO | 2012/011548 A1 | 1/2012 | |
| WO | WO 2012/011548 A1 * | 1/2012 | |

OTHER PUBLICATIONS

Herynk, et al., "The Coordinated Functional Expression of Epidermal Growth Factor Receptor and c-Met in Colorectal Carcinoma Metastasis" *In Vivo*, vol. 14, pp. 587-596 (2000).

Li, et al., "Synthesis and Antitumor Activity of Novel 4-(2-Fluorophenoxy)-quinoline Derivatives Bearing the 4-Oxo-1,4-dihydroquinoline-3-carboxamide Moiety," *Arch. Pharm. Chem. Life Sci.*, vol. 346, pp. 521-533 (2013).

Li, et al., "Discovery of novel 4-(2-fluorophenoxy) quinoline derivatives bearing 4-oxo-1, 4-dihydrocinnoline-3-carboxamide moiety as c-Met kinase inhibitors," *Bioromanic & Medicinal Chemistry*, vol. 21, pp. 2843-2855.

Li, et al., "Design, synthesis and antitumour activity of bisquinoline derivatives connected by 4-oxy-3-fluoroaniline moiety," *European Journal of Medicinal Chemistry*, vol. 64, pp. 62-73 (2013).

Michieli, et al., "Targeting the tumor and its microenvironment by a dual-function decoy Met receptor," *Cancer Cell*, vol. 6, pp. 61-73 (2004).

International Search Report and Written Opinion for International Application No. PCT/CN2012/001640 dated Mar. 7, 2013.

European Search Report for European Patent Application No. 12862344.4 dated Jul. 17, 2015.

* cited by examiner

QUINOLINE AND CINNOLINE DERIVATIVES AND THEIR APPLICATIONS

CROSS-REFERENCE TO RELATED APPLICATIONS

This application is the U.S. National Stage entry of PCT/CN2012/001640, filed Dec. 7, 2012, which claims the benefit of Chinese Patent Application No. 201110453555.8, filed Dec. 30, 2011 and Chinese Patent Application No. 201210111920.1, filed Apr. 17, 2012, the disclosures of each are herein incorporated by reference.

FIELDS OF THE INVENTION

The present invention relates to a new series of quinoline and cinnoline derivatives, pharmaceutically acceptable salts, hydrates, solvates or prodrugs and the processes for their preparation and pharmaceutical compositions containing the compounds. Wherein said quinoline and cinnoline derivatives shows potent inhibitory activity against c-Met kinase. The present invention further relates to the uses of the compounds, pharmaceutically acceptable salts, hydrates, solvates or prodrugs for the preparation of medicaments for the treatment and/or prevention of diseases caused by abnormal expression of c-Met kinase, especially for treatment and/or prevention of cancer.

BACKGROUND OF THE INVENTION

Cancer is a serious hazard to human life and health. With the changes of external factors such as environmental pollution, the number of cancer cases is rising year by year. According to World Health Organization statistics, about 10 million tumor patients are diagnosed worldwide each year currently, and 7 million people die of cancer related diseases, therefore, malignant tumor has become human's second largest killer which is second only to cardiovascular disease.

Protein kinase (PKs), a kind of enzyme, catalyzes phosphorylation of hydroxyl on tyrosine, serine, and threonine residues through the transfer of the end of ATP (γ) phosphate. Through signal transduction pathways, these enzymes regulate cell growth, differentiation and proliferation. Therefore, all aspects of cell cycle are dependent on the activity of PKs substantially. Furthermore, PKs abnormal activity is associated with the host of disease, ranging from relatively non-life threatening diseases (e.g.: psoriasis) to extremely fatal diseases (e.g., glioblastoma). Protein kinases include two types: Protein tyrosine kinase (PTK) and Serine-threonine kinase (STK).

One of the main aspects of PTK activity is to participate as cell-surface protein growth factor receptor. The growth factor receptor turns into an activated form, which interacts with the protein on the inner surface of cell membrane, through combining with growth factor ligand. It leads to phosphorylation of receptor and other protein tyrosine residue, and the formation of multiple cytoplasmic signaling molecule complexes which affects cell reaction, such as division (proliferation), differentiation, growth, metabolism etc.

Growth factor receptor with PTK activity is called receptor tyrosine kinase (RTK), which includes a big family of transmembrane receptor with multiple biological activities. Met is one of the members of this family, and is often referred to as c-Met or human hepatocyte growth factor receptor tyrosine kinase (hHGFR). As a kind of oncogene, the overpass or down regulation of c-Met lead to tumor growth and invasion. Therefore, the expression of c-Met is believed to play a role in tumor cell growth and migration in the early. Stimulated by ligand HGF (also known as Scatter Factor), c-Met starts a variety of physiological processes containing cell proliferation, motility, differentiation, angiogenesis, wound healing, tissue regeneration, embryonic development. Stimulation of hepatocyte growth factor makes c-Met receptor rapidly internalized via clathrin coated vesicles, and gather around cell nucleus by early transportation of endosomes cavity.

Down regulation, dysregulation, overexpression, mutation of c-Met and/or HGF are associated with uncontrolled cell proliferation and survival, which plays an important role in tumor cell invasion, growth and migration in the early. For this reason, c-Met becomes an important target for anticancer drug development.

Overexpression of c-Met and HGF is related to poor diagnosis of prognosis. There is also evidence to support that HGF, as modifier play a role in cancer occurrence, invasion and metastasis (Review: Herynk, M. H. et al. Radinsky, R. (2000) In Vivo 14:587-596). According to latest data, inhibition of tumor growth, survival and invasion is associated with inhibition of the combination between c-Met and HGF and dimerization of c-Met receptor (Michieli et al. (2004) Cancer Cell 6: 61-73). Patents (US 2005/0037431 and US 2004/0166544) describe the inhibition of c-Met in tumor xenotransplantation mouse model to slow down the growth of tumor, and the specific antibodies for c-Met have been expressed to block the binding of HGF to c-Met. The overexpression of c-Met also occurs in NSCLC, small cell lung cancer, lung cancer cell, breast cancer cell, colon cancer cell and prostate cancer cell. Because c-Met seems to play an important role in the formation of multiple tumors, a variety of strategies have been used to inhibit this receptor tyrosine kinase.

By adjusting the HGF β chain binding to c-Met can affect the regulation of HGF/c-Met signaling pathway. In a particular embodiment, zymogen form HGF β mutant shows 14 times lower affinity to c-Met than to wild-type serine protease form, which suggests that comformational change in singlestranded form of cleaved can lead to best interaction. The extensive mutation of active site of serine protease and the active area of HGF β show that among 38 purified double stranded HGF mutants, there are 17 damaged cells moving or phosphorylated but combining with c-Met. However, the decrease of biological activity is associated with the decrease of c-Met binding to its own mutant HGF β mutant, and the elimination of the dominant role of α-chain binding.

Foretinib (Fig. 1), reported as a quinoline compounds, is an oral c-Met and VEGFR/KDR kinase inhibitor with $IC_{50}$ values of 0.4 and 0.8 nM to c-Met and KDR, respectively, and has entered phase II clinical research stage. Clinical studies have shown that, Foretinib showed a significant inhibitory effect against a variety of human tumor cell lines (such as human lung cancer cells, human gastric cancer cells, etc.), with an $IC_{50}$ values of 0.004 μg/mL.

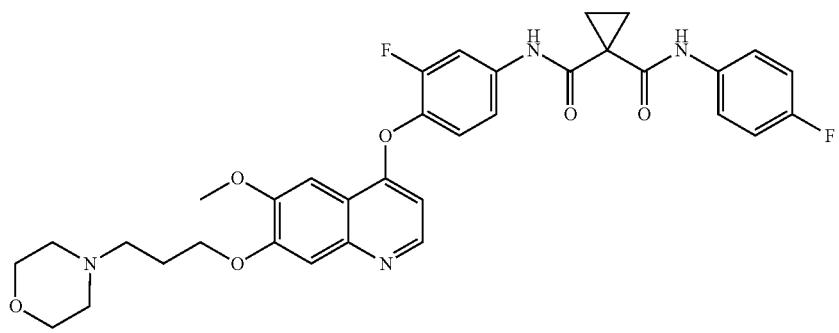

Fig. 1 Foletinib

Based on the prior art references, the inventor designs and synthesizes a new serial of quinoline and cinnoline derivatives, which are shown to possess antitumor activity by in vitro screening assay.

SUMMARY OF THE INVENTION

The present invention relates to a series of quinoline and cinnoline derivatives of general formula I, pharmaceutically acceptable salts, hydrates, solvates or prodrugs thereof,

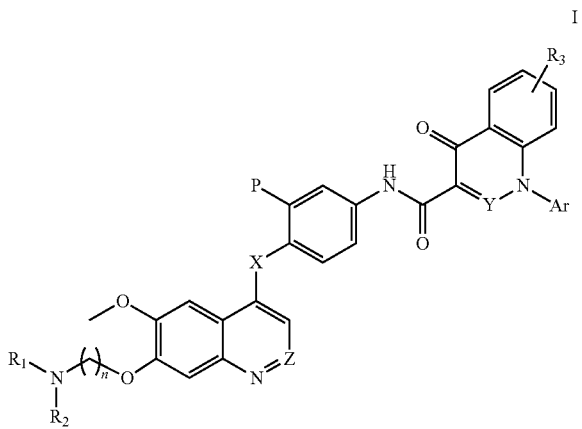

wherein:
P is F or H;
X is O, S, NH or $NCH_3$;
Z is N or CH;
Y is N or CH;
n is an integer between 1 and 6;
$R_1$ and $R_2$ are the same or different and each independently selected from H, $(C_1-C_{10})$ alkyl, $(C_3-C_7)$ cycloalkyl, $(C_2-C_{10})$ alkenyl and $(C_2-C_{10})$alkynyl, and each is optionally substituted with 1 to 3 same or different $R_4$;
Or $R_1$ and $R_2$ are together with the N atom to which they are attached to form 5- to 10-membered heterocyclic radical or 5- to 10-membered heteroaryl radical, optionally substituted with 1 to 4 heteteroatoms each independently selected from N, O, S except the N atom linked by $R_1$ and $R_2$, wherein said the heterocyclic is optionally selected from 1 or 2 carbon-carbon double bond or triple bond and heterocyclic and heteroaryl are optionally substituted with 1 to 3 same or different $R_4$;
$R_4$ is $(C_1-C_4)$alkyl, $(C_1-C_4)$alkoxyl, halogen, hydroxyl, cyano, carboxyl, ester group;

$R_3$ is hydrogen or 1 to 3 substituents selected from hydroxyl, halogen, nitro, amino, cyano, $(C_1-C_6)$alkyl, $(C_1-C_6)$alkenyl, $(C_1-C_6)$ alkynyl, $(C_1-C_6)$ alkoxyl, $(C_1-C_6)$ alkylsulfanyl, $(C_1-C_6)$ alkyl or $(C_1-C_6)$ alkoxyl or $(C_1-C_6)$ alkylsulfanyl is optionally substituted with hydroxyl, amino or halogen, amino is substituted with 1 or 2 $(C_1-C_6)$ alkyl, $(C_1-C_6)$alkylamido, carboxy group which can be free, salts, or form ester group, $(C_1-C_6)$ alkylsulfinyl, sulfonyl, $(C_1-C_6)$ alkylacyl, aminoformyl, aminoformyl substituted with 1 or 2 $(C_1-C_6)$ alkyl, $(C_1-C_3)$alkylenedioxo;
Ar is $(C_6-C_{10})$ aryl, 5- to 10-membered heteroaryl radical, wherein said heteroaryl radical may have 1 to 3 heteroatom(s) each independently selected from N, O, S, and wherein Ar is optionally substituted with 1 to 3 same or different $R_5$;
$R_5$ is hydroxyl, halogen, nitro, amino, cyano, $(C_1-C_6)$ alkyl, $(C_1-C_6)$alkenyl, $(C_1-C_6)$ alkynyl, $(C_1-C_6)$ alkoxyl, $(C_1-C_6)$ alkyl or $(C_1-C_6)$ alkoxyl is optionally substituted with hydroxyl, amino or halogen, amino is substituted with 1 or 2 $(C_1-C_6)$ alkyl, $(C_1-C_6)$alkylamido, carboxy group which can be free, salts, or form ester group, $(C_1-C_6)$ alkylsulfinyl, sulfonyl, $(C_1-C_6)$ alkoxyl $(C_1-C_6)$ alkyl, $(C_1-C_6)$alkylacyl, aminoformyl, aminoformyl is optionally substituted with 1 or 2 $(C_1-C_6)$ alkyl, $(C_1-C_3)$alkylenedioxo. The compound according to claim 1 of formula I, or a pharmaceutically acceptable salts, hydrates, solvates or prodrugs thereof,
Wherein:
P is F;
X is O or NH;
n is an integer between 1 and 4;
$R_1$ and $R_2$ are the same or different and each independently selected from H, $(C_1-C_6)$ alkyl, $(C_3-C_6)$cycloalkyl, $(C_2-C_6)$ alkenyl and $(C_2-C_6)$alkynyl, and each is optionally substituted with 1 to 3 same or different $R_4$;
Or $R_1$ and $R_2$ are together with the N atom to which they are attached to form 5- to 10-membered heterocyclic radical, wherein said heterocyclic radical optionally substituted with 1 to 4 heteteroatoms each independently selected from N, O, S except the N atom linked by $R_1$ and $R_2$, wherein said the heterocyclic is optionally selected from 1 or 2 carbon-carbon double bond or triple bond, wherein heterocyclic is optionally substituted with 1 to 3 same or different $R_4$;
$R_4$ is $(C_1-C_4)$ alkyl, $(C_1-C_4)$alkoxyl, halogen, hydroxyl, cyano, carboxyl, ester group;
$R_3$ is hydrogen or 1 to 3 substituents selected from hydroxyl, halogen, nitro, amino, cyano, $(C_1-C_6)$ alkyl, $(C_1-C_6)$alkenyl, $(C_1-C_6)$ alkynyl, $(C_1-C_6)$ alkoxyl, $(C_1-C_6)$ alkylsulfanyl, $(C_1-C_6)$ alkyl or $(C_1-C_6)$ alkoxyl or $(C_1-C_6)$ alkylsulfanyl is optionally substituted with hydroxyl, amino or halogen, amino is substituted with 1 or 2 $(C_1-C_6)$ alkyl, $(C_1-$ $C_6$)alkylamido, carboxy group which can be free, salts, or form ester group, ($C_1$-$C_6$) alkylsulfinyl, sulfonyl, ($C_1$-$C_6$) alkylacyl, aminoformyl, aminoformyl substituted with 1 or 2 ($C_1$-$C_6$) alkyl, ($C_1$-$C_3$)alkylenedioxo;

Ar is ($C_6$-$C_{10}$) aryl, 5- to 10-membered heteroaryl radical, wherein said heteroaryl radical may have 1 to 3 heteroatom(s) each independently selected from N, O, S, and wherein Ar is optionally substituted with 1 to 3 same or different $R_5$;

$R_5$ is hydroxyl, halogen, nitro, amino, cyano, ($C_1$-$C_6$) alkyl, ($C_1$-$C_6$)alkenyl, ($C_1$-$C_6$) alkynyl, ($C_1$-$C_6$) alkoxyl, ($C_1$-$C_6$) alkyl or ($C_1$-$C_6$) alkoxyl is optionally substituted with hydroxyl, amino or halogen, amino is substituted with 1 or 2 ($C_1$-$C_6$) alkyl, ($C_1$-$C_6$)alkylamido, carboxy group which can be free, salts, or form ester group, ($C_1$-$C_6$) alkylsulfinyl, sulfonyl, ($C_1$-$C_6$) alkoxyl ($C_1$-$C_6$) alkyl, ($C_1$-$C_6$)alkylacyl, aminoformyl, aminoformyl is optionally substituted with 1 or 2 ($C_1$-$C_6$) alkyl, ($C_1$-$C_3$)alkylenedioxo.

The compound according to claim 1 of formula I, or a pharmaceutically acceptable salts, hydrates, solvates or prodrugs thereof, Wherein:
P is F;
X is O;
Z is N, CH;
Y is N, CH;
n is an integer between 1 and 4;
$R_1$ and $R_2$ are the same or different and each independently selected from H, ($C_1$-$C_6$) alkyl, ($C_3$-$C_6$)cycloalkyl, ($C_2$-$C_6$) alkenyl and ($C_2$-$C_6$)alkynyl, and each is optionally substituted with 1 to 3 same or different $R_4$;

Or $R_1$ and $R_2$ are together with the N atom to which they are attached to form 5- to 10-membered heterocyclic radical, wherein said heterocyclic radical optionally substituted with 1 to 4 heteteroatoms each independently selected from N, O, S except the N atom linked by $R_1$ and $R_2$, wherein said the heterocyclic is optionally selected from 1 or 2 carbon-carbon double bond or triple bond, wherein heterocyclic is optionally substituted with 1 to 3 same or different $R_4$;

$R_4$ is ($C_1$-$C_4$) alkyl, ($C_1$-$C_4$)alkoxyl, halogen, hydroxyl, cyano, carboxyl, ester group;

$R_3$ is hydrogen or 1 to 3 substituents selected from hydroxyl, halogen, nitro, amino, cyano, ($C_1$-$C_6$) alkyl, ($C_1$-$C_6$)alkenyl, ($C_1$-$C_6$) alkynyl, ($C_1$-$C_6$) alkoxyl, ($C_1$-$C_6$) alkylsulfanyl, ($C_1$-$C_6$) alkyl or ($C_1$-$C_6$) alkoxyl or ($C_1$-$C_6$) alkylsulfanyl is optionally substituted with hydroxyl, amino or halogen, amino is substituted with 1 or 2 ($C_1$-$C_6$) alkyl, ($C_1$-$C_6$)alkylamido, carboxy group which can be free, salts, or form ester group, ($C_1$-$C_6$) alkylsulfinyl, sulfonyl, ($C_1$-$C_6$) alkylacyl, aminoformyl, aminoformyl substituted with 1 or 2 ($C_1$-$C_6$) alkyl, ($C_1$-$C_3$)alkylenedioxo;

Ar is phenyl, naphthyl, 5- to 10-membered heteroaryl radical, wherein said heteroaryl radical may have 1 to 3 heteroatom(s) each independently selected from N, O, S, and wherein Ar is optionally substituted with 1 to 3 same or different $R_5$;

$R_5$ is hydroxyl, halogen, nitro, amino, cyano, ($C_1$-$C_6$) alkyl, ($C_1$-$C_6$)alkenyl, ($C_1$-$C_6$) alkynyl, ($C_1$-$C_6$) alkoxyl, ($C_1$-$C_6$) alkyl or ($C_1$-$C_6$) alkoxyl is optionally substituted with hydroxyl, amino or halogen, amino is substituted with 1 or 2 ($C_1$-$C_6$) alkyl, ($C_1$-$C_6$)alkylamido, carboxy group which can be free, salts, or form ester group, ($C_1$-$C_6$) alkylsulfinyl, sulfonyl, ($C_1$-$C_6$) alkoxyl ($C_1$-$C_6$) alkyl, ($C_1$-$C_6$)alkylacyl, aminoformyl, aminoformyl is optionally substituted with 1 or 2 ($C_1$-$C_6$) alkyl, ($C_1$-$C_3$)alkylenedioxo.

The compound according to claim 1 of formula I, or a pharmaceutically acceptable salts, hydrates, solvates or prodrugs thereof, Wherein:
P is F;
X is O;
Z is N, CH;
Y is N, CH;
n is an integer between 1 and 4;
$R_1$ and $R_2$ are together with the N atom to which they are attached to form 5- to 6-membered heterocyclic radical, wherein said heterocyclic radical optionally substituted with 1 to 4 heteteroatoms each independently selected from N, O, S except the N atom linked by $R_1$ and $R_2$, wherein said the heterocyclic is optionally selected from 1 or 2 carbon-carbon double bond or triple bond, wherein heterocyclic radicals are optionally substituted with 1 to 3 same or different $R_4$;

$R_4$ is ($C_1$-$C_4$)alkyl;

$R_3$ is hydrogen or 1 to 3 substituent(s) optionally selected from halogen, ($C_1$-$C_4$) alkyl, ($C_1$-$C_4$) alkoxyl, trifluoromethyl, trifluoromethoxy;

Ar is phenyl, naphthyl, 5- to 10-membered heteroaryl radical, wherein said heteroaryl radical may have 1 to 3 heteroatom(s) each independently selected from N, O, S, and wherein Ar is optionally substituted with 1 to 3 same or different $R_5$;

$R_5$ is halogen, ($C_1$-$C_4$) alkyl, ($C_1$-$C_4$) alkoxyl, ($C_1$-$C_4$) alkyl or ($C_1$-$C_4$) alkoxyl optionally substituted with halogen, amino is substituted with 1 or 2 ($C_1$-$C_6$) alkyl, ($C_1$-$C_4$) alkoxyl($C_1$-$C_4$) alkyl, ($C_1$-$C_6$)alkylacyl, aminoformyl, aminoformyl is substituted with 1 or 2 ($C_1$-$C_6$) alky, ($C_1$-$C_3$) alkylenedioxo.

The compound according to claim 1 of formula I, or a pharmaceutically acceptable salts, hydrates, solvates or prodrugs thereof, Wherein:
P is F;
X is O;
Z is N, CH;
Y is N, CH;
n is an integer between 1 and 4;
$R_1$ and $R_2$ are together with the N atom to which they are attached to form 1-piperidino, 4-morpholino, 4-methyl-1-piperazinyl, 4-methyl-1-piperidino, 1-pyrrolidinyl;

$R_3$ is hydrogen or 1 to 3 substituent(s) optionally selected from halogen, ($C_1$-$C_4$) alkyl, ($C_1$-$C_4$) alkoxyl, trifluoromethyl, trifluoromethoxy;

Ar is phenyl, and Ar is optionally substituted with 1 to 3 same or different $R_5$;

$R_5$ is halogen, ($C_1$-$C_4$) alkyl, ($C_1$-$C_4$) alkoxyl, ($C_1$-$C_4$) alkyl or ($C_1$-$C_4$) alkoxyl optionally substituted with halogen, amino is substituted with 1 or 2 ($C_1$-$C_6$) alkyl, ($C_1$-$C_4$) alkoxyl($C_1$-$C_4$) alkyl, ($C_1$-$C_6$)alkylacyl, aminoformyl, aminoformyl is substituted with 1 or 2 ($C_1$-$C_6$) alky, ($C_1$-$C_3$) alkylenedioxo.

The compound according to claim 1 of formula I, or a pharmaceutically acceptable salts, hydrates, solvates or prodrugs thereof, Wherein:
P is F;
X is O;
Z is CH;
Y is N;
n is 3;
$R_3$ is hydrogen;
$R_1$ and $R_2$ are together with the N atom to which they are attached to form 1-piperidino, 4-morpholino, 4-methyl-1-piperazinyl, 4-methyl-1-piperidino, 1-pyrrolidinyl;

Ar is phenyl, and wherein Ar is optionally substituted with 1 to 3 same or different $R_5$;

R₅ is halogen, $(C_1-C_4)$ alkyl, $(C_1-C_4)$ alkoxyl, trifluoromethyl and trifluoromethoxy;

Especially F, Cl and trifluoromethyl.

The compound according to claim 1 of formula I, or a pharmaceutically acceptable salts, hydrates, solvates or prodrugs thereof, wherein the compound of general formula I is selected from the following compounds, but these compounds are not means any limit to this invention:

N-(3-fluoro-4-((6-methoxy-7-(3-(pyrrolidin-1-yl)propoxy)quinolin-4-yl)oxy)phenyl)-1-(2-(trifluoromethyl)phenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2-chlorophenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(4-bromophenyl)-4-oxo-1,4-dihydrocinnoline-3-carboxamide;

N-(3-fluoro-4-((6-methoxy-7-(3-(morpholin-4-ylpropoxy)quinolin-4-yl)oxy)phenyl)-1-(2-(trifluoromethyl)phenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2-(trifluoromethyl)phenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(3-(trifluoromethyl)phenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2-fluorophenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2-(trifluoromethyl)phenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(3-fluorophenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(4-chlorophenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(3,4-difluorophenyl)-4-oxo-1,4-dihydrocinnoline-3-carboxamide;

N-(3-fluoro-4-((6-methoxy-7-(3-(pyrrolidin-1-yl)propoxy)quinolin-4-yl)oxy)phenyl)-1-(3,4-difluorophenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(4-fluorophenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(2-fluorophenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(2-chlorophenyl)-4-oxo-1,4-dihydrocinnoline-3-carboxamide;

N-(3-fluoro-4-((6-methoxy-7-(3-(pyrrolidin-1-yl)propoxy)quinolin-4-yl)oxy)phenyl)-1-(2-chlorophenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2-chlorophenyl)-4-oxo-1,4-dihydrocinnoline-3-carboxamide;

N-(3-fluoro-4-((6-methoxy-7-(3-(pyrrolidin-1-yl)propoxy)quinolin-4-yl)oxy)phenyl)-1-(2-bromo-4-fluorophenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2-bromo-4-fluorophenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2-chloro-5-(trifluoromethyl)phenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(2-chloro-5-(trifluoromethyl)phenyl)-4-oxo-1,4-dihydrocinnoline-3-carboxamide;

N-(3-fluoro-4-((6-methoxy-7-(3-(pyrrolidin-1-yl)propoxy)quinolin-4-yl)oxy)phenyl)-1-(2-chloro-5-(trifluoromethyl)phenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2-chloro-5-(trifluoromethyl)phenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(2,4-dimethylphenyl)-4-oxo-1,4-dihydrocinnoline-3-carboxamide;

N-(3-fluoro-4-((6-methoxy-7-(3-(pyrrolidin-1-yl)propoxy)quinolin-4-yl)oxy)phenyl)-1-(2,4-dimethylphenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2,4-dimethylphenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2,4-dichlorophenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(2,4-dichlorophenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2,6-dichlorophenyl)-4-oxo-1,4-dihydrocinnoline-3-carboxamide;

N-(3-fluoro-4-((6-methoxy-7-(3-(4-methylpiperidin-1-yl)propoxy)quinolin-4-yl)oxy)phenyl)-1-(2,6-dichlorophenyl)-4-oxo-1,4-dihydrocinnoline-3-carboxamide;

N-(3-fluoro-4-((6-methoxy-7-(3-(pyrrolidin-1-yl)propoxy)quinolin-4-yl)oxy)phenyl)-1-(2,6-dichlorophenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2,6-dichlorophenyl)-4-oxo-1,4-dihydrocinnoline-3-carboxamide;

N-(3-fluoro-4-((6-methoxy-7-(3-(-(morpholin-4-yl)propoxy)quinolin-4-yl)oxy)phenyl)-1-(2-chlorophenyl)-4-oxo-1,4-dihydrocinnoline-3-carboxamide;

N-(3-fluoro-4-((6-methoxy-7-(3-(morpholin-4-yl)propoxy)quinolin-4-yl)oxy)phenyl)-1-(2-bromophenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(2-bromophenyl)-4-oxo-1,4-dihydrocinnoline-3-carboxamide;

N-(3-fluoro-4-((6-methoxy-7-(3-(-(morpholin-4-yl)propoxy)quinolin-4-yl)oxy)phenyl)-1-(4-fluorophenyl)-4-oxo-1,4-dihydrocinnoline-3-carboxamide;

N-(3-fluoro-4-((6-methoxy-7-(3-(morpholin-4-yl)propoxy)quinolin-4-yl)oxy)phenyl)-1-(2-(trifluoromethoxy)phenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2-(trifluoromethoxy)phenyl)-4-oxo-1,4-dihydrocinnoline-3-carboxamide;

N-(3-fluoro-4-((6-methoxy-7-(3-(morpholin-4-yl)propoxy)quinolin-4-yl)oxy)phenyl)-1-(4-bromophenyl)-4-oxo-1,4-dihydrocinnoline-3-carboxamide;

N-(3-fluoro-4-((6-methoxy-7-(3-(4-methylpiperazin-1-yl)propoxy)quinolin-4-yl)oxy)phenyl)-1-(4-bromophenyl)-4-oxo-1,4-dihydrocinnoline-3-carboxamide;

N-(3-fluoro-4-((6-methoxy-7-(3-(pyrrolidin-1-yl)propoxy)
quinolin-4-yl)oxy)phenyl)-1-(2-fluorophenyl)-4-oxo-1,4-
dihydrocinnoline-3-carboxamide;

N-(3-fluoro-4-((6-methoxy-7-(3-(4-methylpiperazin-1-yl)
propoxy)quinolin-4-yl)oxy)phenyl)-1-(4-fluorophenyl)-
4-oxo-1,4-dihydrocinnoline-3-carboxamide;

N-(3-fluoro-4-((6-methoxy-7-(3-(4-methylpiperazin-1-yl)
propoxy)quinolin-4-yl)oxy)phenyl)-1-(2,4-dichlorophe-
nyl)-4-oxo-1,4-dihydrocinnoline-3-carboxamide;

7-F—N-(3-fluoro-4-((6-methoxy-7-(3-(4-methylpiperazin-
1-yl)propoxy)quinolin-4-yl)oxy)phenyl)-1-(2-(trifluo-
romethyl)phenyl)-4-oxo-1,4-dihydrocinnoline-3-car-
boxamide;

7-F—N-(3-fluoro-4-((6-methoxy-7-(3-(morpholin-4-yl)pro-
poxy)quinolin-4-yl)oxy)phenyl)-1-(2-fluorophenyl)-4-
oxo-1,4-dihydrocinnoline-3-carboxamide.

The compound of general formula I according to claim 1, pharmaceutically acceptable salts, hydrates, solvates or prodrugs thereof, N-(3-fluoro-4-((6-methoxy-7-(3-(4-methylpiperazin-1-yl)
propoxy)quinolin-4-yl)oxy)phenyl)-1-(4-fluorophenyl)-
4-oxo-1,4-dihydroquinoline-3-carboxamide;

N-(3-fluoro-4-((6-methoxy-7-(3-(4-methylpiperidin-1-yl)
propoxy)quinolin-4-yl)oxy)phenyl)-1-(2-fluorophenyl)-
4-oxo-1,4-dihydroquinoline-3-carboxamide;

N-(3-fluoro-4-((6-methoxy-7-(3-(morpholin-4-yl)propoxy)
quinolin-4-yl)oxy)phenyl)-4-oxo-1-(2-(trifluoromethyl)
phenyl)-1,4-dihydroquinoline-3-carboxamide;

N-(3-fluoro-4-((6-methoxy-7-(3-(piperidin-1-yl)propoxy)
quinolin-4-yl)oxy)phenyl)-1-(4-fluorophenyl)-4-oxo-1,4-
dihydroquinoline-3-carboxamide;

N-(3-fluoro-4-((6-methoxy-7-(3-(piperidin-1-yl)propoxy)
quinolin-4-yl)oxy)phenyl)-1-(2-fluorophenyl)-4-oxo-1,4-
dihydroquinoline-3-carboxamide;

N-(3-fluoro-4-((6-methoxy-7-(3-(pyrrolidin-1-yl)propoxy)
quinolin-4-yl)oxy)phenyl)-1-(2-fluorophenyl)-4-oxo-1,4-
dihydroquinoline-3-carboxamide;

N-(3-fluoro-4-((6-methoxy-7-(3-(4-methylpiperazin-1-yl)
propoxy)quinolin-4-yl)oxy)phenyl)-1-(2-fluorophenyl)-
4-oxo-1,4-dihydroquinoline-3-carboxamide;

N-(3-fluoro-4-((6-methoxy-7-(3-(piperidin-1-yl)propoxy)
quinolin-4-yl)oxy)phenyl)-1-(2-chlorophenyl)-4-oxo-1,4-
dihydroquinoline-3-carboxamide;

N-(3-fluoro-4-((6-methoxy-7-(3-(4-methylpiperidin-1-yl)
propoxy)quinolin-4-yl)oxy)phenyl)-1-(2-chlorophenyl)-
4-oxo-1,4-dihydroquinoline-3-carboxamide;

N-(3-fluoro-4-((6-methoxy-7-(3-(pyrrolidin-1-yl)propoxy)
quinolin-4-yl)oxy)phenyl)-1-(2-chlorophenyl)-4-oxo-1,4-
dihydroquinoline-3-carboxamide;

N-(3-fluoro-4-((6-methoxy-7-(3-(4-methylpiperazin-1-yl)
propoxy)quinolin-4-yl)oxy)phenyl)-1-(2-chlorophenyl)-
4-oxo-1,4-dihydroquinoline-3-carboxamide;

N-(3-fluoro-4-((6-methoxy-7-(3-(4-methylpiperidin-1-yl)
propoxy)quinolin-4-yl)oxy)phenyl)-4-oxo-1-(2-(trifluo-
romethyl)phenyl)-1,4-dihydroquinoline-3-carboxamide;

N-(3-fluoro-4-((6-methoxy-7-(3-(4-methylpiperidin-1-yl)
propoxy)quinolin-4-yl)oxy)phenyl)-1-(3,4-difluorophe-
nyl)-4-oxo-1,4-dihydroquinoline-3-carboxamide;

N-(3-fluoro-4-((6-methoxy-7-(3-(piperidin-1-yl)propoxy)
quinolin-4-yl)oxy)phenyl)-1-(3,4-difluorophenyl)-4-oxo-
1,4-dihydroquinoline-3-carboxamide.

The compound of general formula I according to claim 1, pharmaceutically acceptable salts, hydrates, solvates or prodrugs thereof:

N-(3-fluoro-4-((6-methoxy-7-(3-(4-methylpiperazin-1-yl)
propoxy)quinolin-4-yl)oxy)phenyl)-1-(4-fluorophenyl)-
4-oxo-1,4-dihydroquinoline-3-carboxamide;

N-(3-fluoro-4-((6-methoxy-7-(3-(4-methylpiperidin-1-yl)
propoxy)quinolin-4-yl)oxy)phenyl)-1-(2-fluorophenyl)-
4-oxo-1,4-dihydroquinoline-3-carboxamide;

N-(3-fluoro-4-((6-methoxy-7-(3-(morpholin-4-yl)propoxy)
quinolin-4-yl)oxy)phenyl)-4-oxo-1-(2-(trifluoromethyl)
phenyl)-1,4-dihydroquinoline-3-carboxamide;

N-(3-fluoro-4-((6-methoxy-7-(3-(piperidin-1-yl)propoxy)
quinolin-4-yl)oxy)phenyl)-1-(4-fluorophenyl)-4-oxo-1,4-
dihydroquinoline-3-carboxamide;

N-(3-fluoro-4-((6-methoxy-7-(3-(piperidin-1-yl)propoxy)
quinolin-4-yl)oxy)phenyl)-1-(2-fluorophenyl)-4-oxo-1,4-
dihydroquinoline-3-carboxamide;

N-(3-fluoro-4-((6-methoxy-7-(3-(pyrrolidin-1-yl)propoxy)
quinolin-4-yl)oxy)phenyl)-1-(2-fluorophenyl)-4-oxo-1,4-
dihydroquinoline-3-carboxamide;

N-(3-fluoro-4-((6-methoxy-7-(3-(4-methylpiperazin-1-yl)
propoxy)quinolin-4-yl)oxy)phenyl)-1-(2-fluorophenyl)-
4-oxo-1,4-dihydroquinoline-3-carboxamide;

N-(3-fluoro-4-((6-methoxy-7-(3-(piperidin-1-yl)propoxy)
quinolin-4-yl)oxy)phenyl)-1-(2-chlorophenyl)-4-oxo-1,4-
dihydroquinoline-3-carboxamide;

N-(3-fluoro-4-((6-methoxy-7-(3-(4-methylpiperidin-1-yl)
propoxy)quinolin-4-yl)oxy)phenyl)-1-(2-chlorophenyl)-
4-oxo-1,4-dihydroquinoline-3-carboxamide;

N-(3-fluoro-4-((6-methoxy-7-(3-(pyrrolidin-1-yl)propoxy)
quinolin-4-yl)oxy)phenyl)-1-(2-chlorophenyl)-4-oxo-1,4-
dihydroquinoline-3-carboxamide;

According to some general methods involved in the field of the invention, the term "pharmaceutically acceptable salts" as used herein refer to a pharmaceutically acceptable salt formed by quinoline and cinnoline derivatives defined as formula I reacted with acid. The acid includes inorganic or organic acids, and those salts formed by using the following acids are especially preferable: hydrochloric acid, hydrobromic acid, sulphuric acid, phosphoric acid, methanesulfonic acid, ethanesulfonic acid, toluenesulfonic acid, benzenesulfonic acid, naphthalene disulfonic acid, acetic acid, propionic acid, lactic acid, trifluoroacetic acid, maleic acid, citric acid, fumaric acid, oxalic acid, tartaric acid or benzoic acid.

In addition, the present invention includes the prodrugs of the derivatives of present invention. According to present invention, the prodrugs are the derivatives of general formula I, and the prodrugs have low biological activity or even have no biological activity, but which can be converted to a corresponding biologically-active form (e.g. by metabolism, solvolysis or other ways) under physiological conditions upon administration.

In addition, the present invention includes the prodrugs of the derivatives of present invention. According to present invention, the prodrugs are the derivatives of general formula I, and the prodrugs have low biological activity or even have no biological activity, but which can be converted to a corresponding biologically-active form (e.g. by metabolism, solvolysis or other ways) under physiological conditions upon administration.

Unless indicated otherwise, the term "halogen" refers to fluorine, chlorine, bromine or iodine atom; "alkyl" refers to a straight or branched alkyl; "alkylene" refers to a straight or branched alkylene; "cycloalkyl" refers to substituted or unsubstituted cycloalkyl; "aryl" refers to unsubstituted or substituted phenyl; "heteroaryl" comprises one or more heteroatoms selected from O, N and S, and may be one or more rings, and the ring system is aromatic and can be exemplified by imidazolyl, pyridinyl, pyrazolyl, (1,2,3)- and (1,2,4)-triazolyl, furanyl, thienyl, pyrrolyl, thiazolyl, benzothiazolyl, oxazolyl, isoxazolyl, naphthyl, quinolyl, isoquinolyl, benzimidazolyl, benzoxazolyl and the like. "Saturated or partially saturated heterocyclic group" refers to groups containing one or more heteroatoms selected from N, O, S monocyclic or polycyclic ring system, such as pyrrolidinyl, morpholinyl, piperazinyl, piperidinyl, pyrazolidinyl, imidazolidinyl and thiazolyl group.

The present invention further relates to a pharmaceutical composition, comprising quinoline and cinnoline derivatives as shown by general formula I, and pharmaceutically acceptable salts, hydrates, solvates or prodrug thereof as active ingredient, and pharmaceutically acceptable carrier or excipients if necessary. The pharmaceutically acceptable excipients refer to any diluents, adjuvants and/carrier that can be usable in pharmaceutical field. The derivatives in this present invention can be combined with other active ingredients as long as they are not deleterious to the recipient thereof, such as allergic action.

The clinical dose of quinoline and cinnoline derivatives of formula I required to be effective, will, of course, be varied. The factors to be considered include the therapeutic efficacy and bioavailability in vivo of the active ingredients, the rate of metabolism and discretion of them, the patient's age, sex and the period of disease. However, a suitable effective dose is in the range of about 10 to 1000 mg per day, preferably in the range about 50 to 500 mg per day. So, When the pharmaceutical compositions of the invention are formulated in a unit dosage form, considering the effective dose mentioned above, the amount of quinoline and cinnoline derivatives of formula I contained in each unit of pharmaceutical preparation is in the range of about 10 to 500 mg, preferably in the range of about 50 to 300 mg. According to the instructions of doctors or physician, the preparation can be administered several times at intervals (preferable once to six times).

The pharmaceutical composition of present invention could be prepared into various formulations comprising several excipients commonly used in the pharmaceutical art, for example, injectable formulation, tablet, capsule, aerosol, suppository, membrane, guttate pills, linimentum, ointment and so on.

The carrier useful for the pharmaceutical composition of present invention is those commonly used in the pharmaceutical field, including adhesive, lubricant, disintegrating agent, cosolvent, diluents, stabilizer, suspending agent, pigment, flavoring agent, preservatives, diluent sand matrix. The pharmaceutical formulation may be administrated by oral or parenteral pathway (e.g. intravenous, subcutaneous, intraperitoneal or topical), and could be prepared into enteric coated tablet in case some medicines are unstable in the conditions of stomach.

The active compounds or pharmaceutically acceptable salts or solvates of the present invention thereof can be used for the only antiproliferative drug alone, or be combined with already listed antiproliferative drug for the treatment and/or prevention of proliferative diseases, such as psoriasis, benign prostatic hypertrophy, atherosclerosis and restenosis.

We have found the compounds of present invention have an inhibitory activity on tumor cell growth. Hence, the compounds can be useful for the preparation of medicaments for treating and/or preventing cancer diseases, such as breast, lung, liver, kidney, colon, rectum, stomach, prostate, bladder, uterus, pancreas, bone marrow, testes, ovaries, lymph node, soft tissue, head and neck, thyroid, esophageal, leukemia, neurocytoma and so on.

According to the test against H460 (human lung cancer), HT-29 (human colon cancer), U87MG (human glioblastoma), MKN-45 (human gastric cancer) and SMMC-7721 (human liver cancer), compounds of the present invention showed significant inhibition on lung cancer, colon cancer and gastric cancer cell lines. Therefore, the said compounds can be especially useful for the preparation of medicaments for treating and/or preventing of lung cancer and colon cancer.

According to the test against c-Met, compounds of the present invention showed significant inhibition to c-Met kinase, and showed potent inhibition to lung cancer cells, colon cancer cells with high expression of c-Met. Therefore, the said compounds can be especially useful for the preparation of medicaments for treating and/or preventing of lung cancer.

The active compounds, pharmaceutically acceptable salts or solvates of the present invention may be used as a single anticancer medicament, or used in combination with anticancer drugs listed (Platinum drug, cisplatin; camptothecin drug irinotecan; vinca alkaloid drug, Navelbine; deoxycytidine celecoxib drug, gemcitabine; etoposide, paclitaxel, etc.). Such a combined therapy can be achieved by administrating respective therapeutic components simultaneously, subsequently or separately.

The following Examples and Preparation Examples are provided to further illustrate and exemplify the compounds of the invention and preparation methods thereof. It shall not be understood that the following Examples and Preparation are intended to limit the scope of the invention in any way.

The following Route 1 illustrates the preparation of the compounds of general formula I of the present invention, wherein all starting materials can be prepared by the methods depicted in the Schemes or the methods well known to one of ordinary skill in the organic chemistry art, or are commercially available. All of the final compounds of the present invention are prepared by the methods depicted in the Schemes or similar methods, and these methods are well known to one of ordinary skill in the organic chemistry art. All variable factors as involved in these Schemes are defined as follows or defined as in claims.

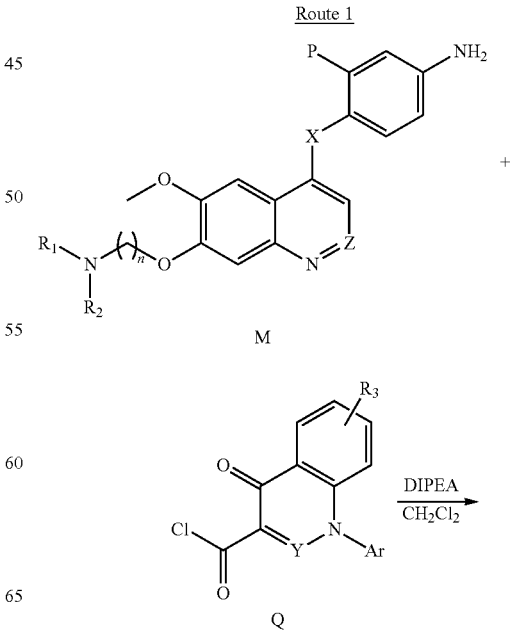

13

-continued

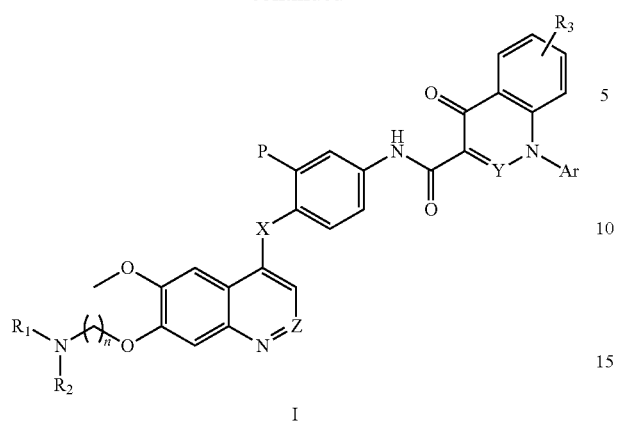

I

The derivatives of general formula I in this invention are obtained by substitution reaction using the corresponding intermediates M and Q as illustrated in Route 1.

2. The compounds of general formula I in this invention, when X is O and Z is CH, then intermediates M-1 are prepared according to the method in Route 2. Other substituents are defined as claims in this invention.

Route 2

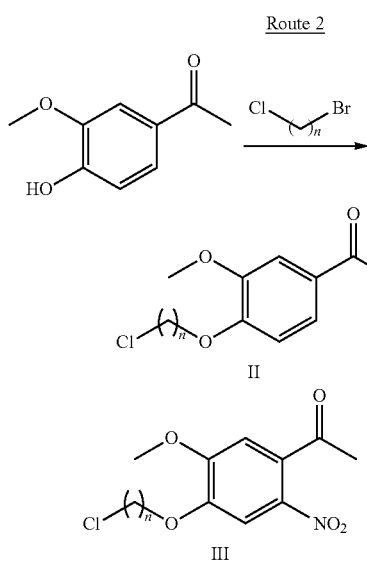

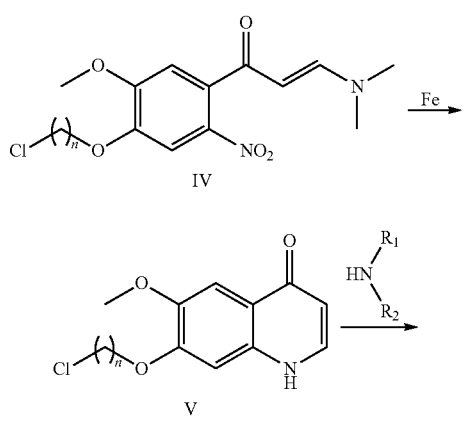

14

-continued

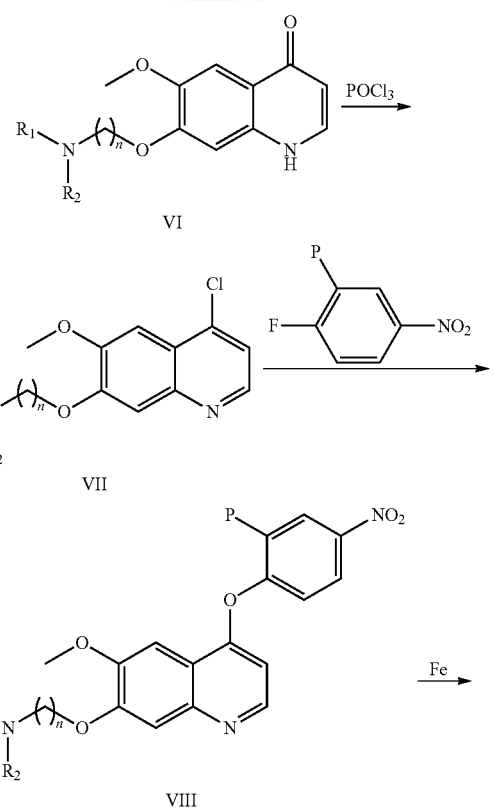

When X is O, and Z is N, then compounds M-2 are prepared according to the method in Route 3. Other substituents are defined as claims in this invention.

Route 3

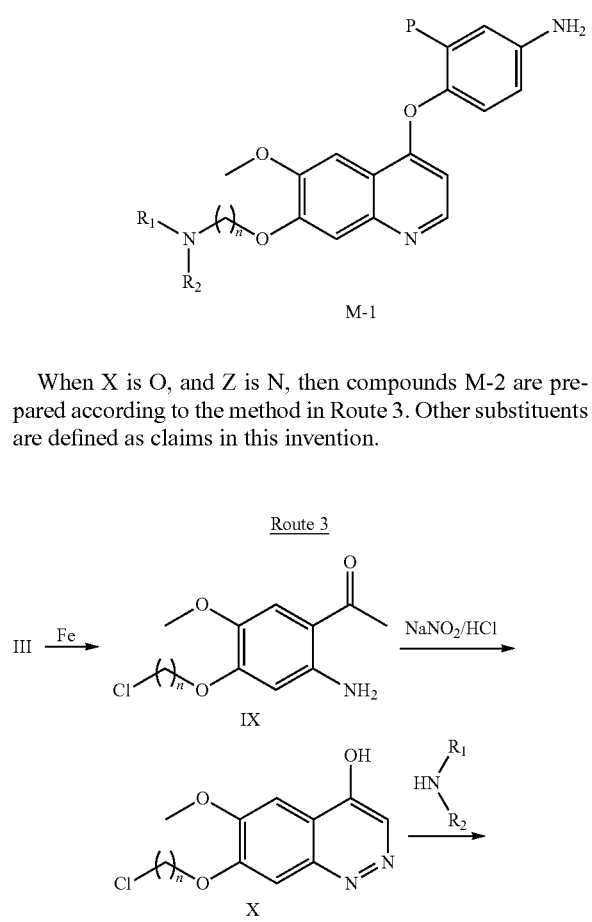

-continued

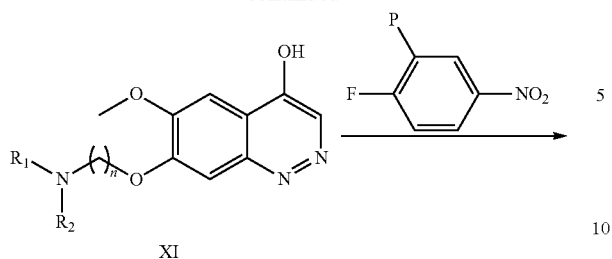

XI

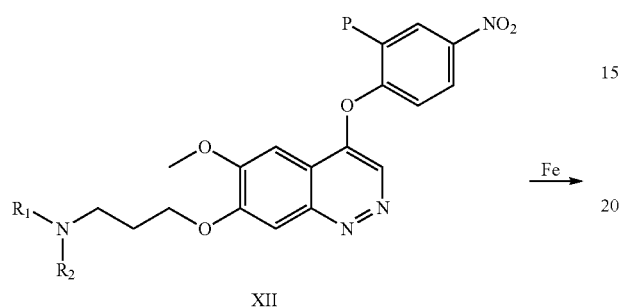

XII

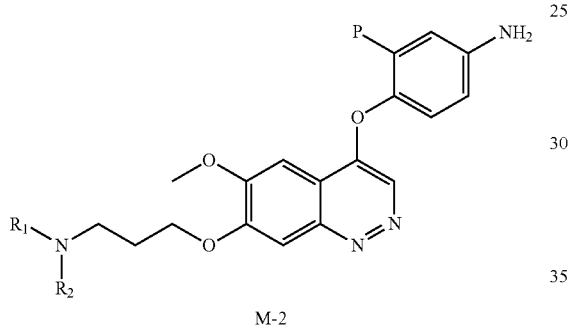

M-2

When X is S, and Z is CH, the compounds M-3 are prepared by substitution reaction using intermediate VII in Route 2 and 2-fluoro-4-nitrobenzene thiophenol, followed by reduction reaction.

When X is S, and Z is N, then compounds M-4 are prepared by chlorine substitution reaction using intermediate XI in Route 3, followed by substitution reaction with 2-fluoro-4-nitrobenzene thiophenol and reduction reaction.

When X is NH, and Z is CH, then compounds M-5 are prepared by substitution reaction using intermediate VII in Route 2 and 2-fluoro-4-nitroaniline, followed by reduction reaction.

When X is NH, and Z is N, then compounds M-6 are prepared by chlorine substitution reaction using intermediate XI in Route 3, followed by substitution reaction with 2-fluoro-4-nitroaniline and reduction reaction.

When Y is N, then intermediates Q-1 are prepared according to the method in Route 4.

Route 4

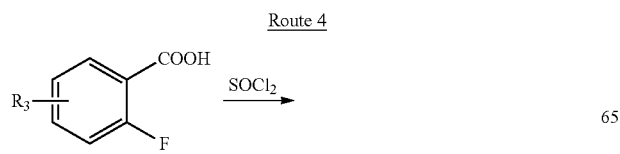

-continued

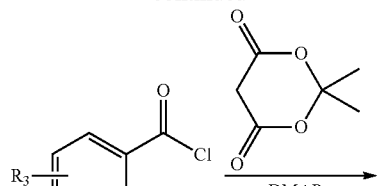
a

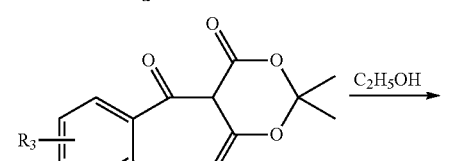
b

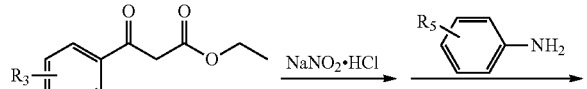
c

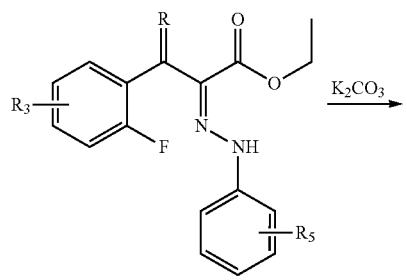
d

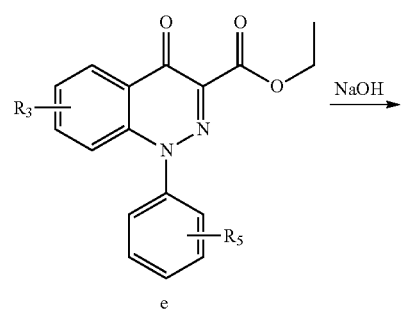
e

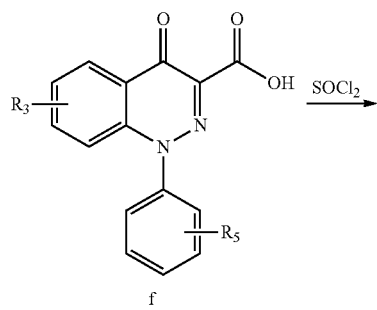
f

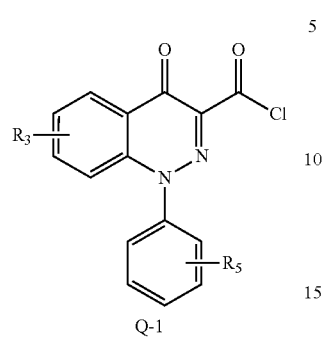

Q-1

When Y is CH, then intermediates Q-2 are prepared according to the method in Route 5.

Route 5

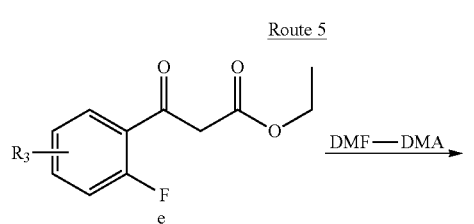

e

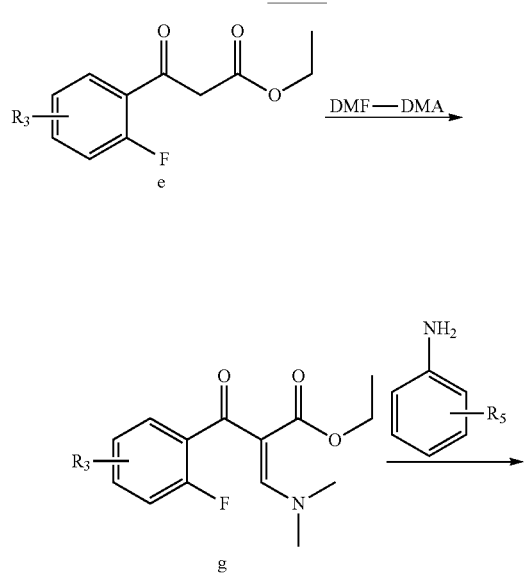

g h

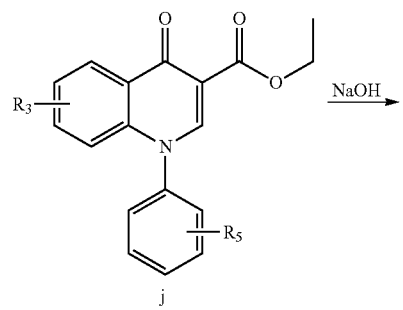

j

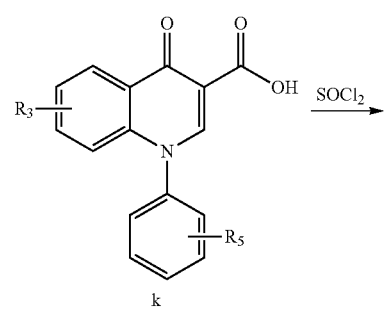

k

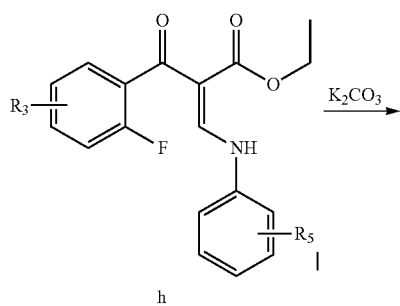

Q-2

In those five routes, all substitutes including $R_1$, $R_2$, $R_3$, and $R_5$ in all intermediates are defined as claims in this invention.

EMBODIMENTS

The following Examples aim to illustrate rather than limit the scope of the invention. The nuclear magnetic resonance hydrogen spectrum (HNMR) of the produced compounds of the invention was determined by Bruker ARX-600 (Supplied by Leaman China), and mass spectrum (MS) was determined by Agilent 1100 LC/MSD (Supplied by Agilent China); all reagents were analytically pure or chemically pure.

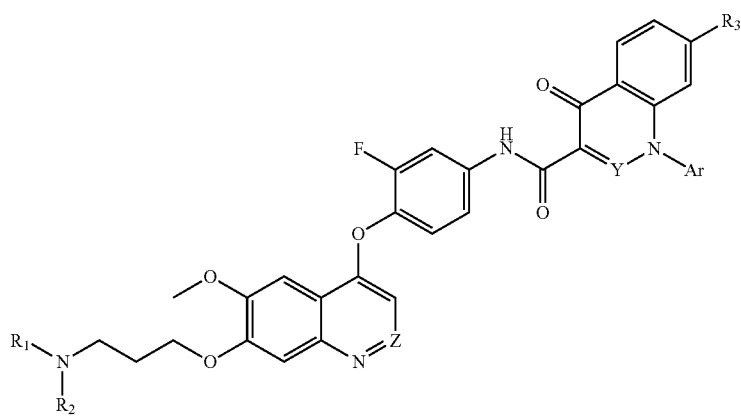
| Example | —NR₁R₂ | Y | Z | R₃ | Ar |
|---|---|---|---|---|---|
| Example 1 | pyrrolidin-1-yl | N | CH | H | 2-CF₃-phenyl |
| Example 2 | piperidin-1-yl | N | CH | H | 2-Cl-phenyl |
| Example 3 | piperidin-1-yl | N | CH | H | 4-Br-phenyl |
| Example 4 | morpholin-4-yl | N | CH | H | 2-CF₃-phenyl |
| Example 5 | piperidin-1-yl | N | CH | F | 2-CF₃-phenyl |
| Example 6 | piperidin-1-yl | N | CH | H | 3-CF₃-phenyl |

-continued
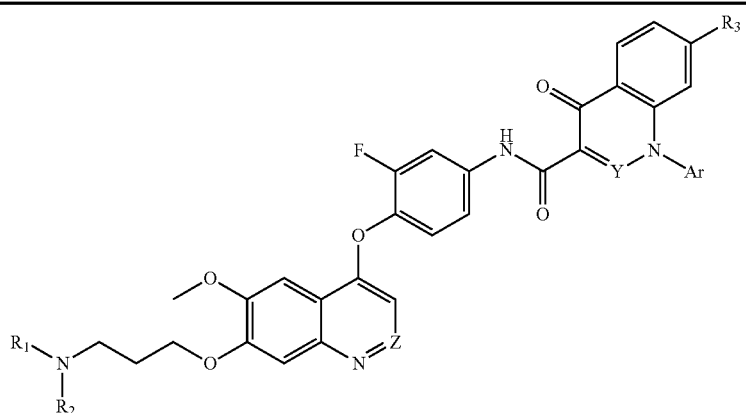
| Example | —NR₁R₂ | Y | Z | R₃ | Ar |
|---|---|---|---|---|---|
| Example 7 | piperidinyl | N | CH | H | 2-F-phenyl |
| Example 8 | 4-methylpiperazinyl | N | CH | H | 2-CF₃-phenyl |
| Example 9 | piperidinyl | N | CH | H | 3-F-phenyl |
| Example 10 | piperidinyl | N | CH | H | 4-Cl-phenyl |
| Example 11 | piperidinyl | N | CH | H | 3,4-diF-phenyl |
| Example 12 | pyrrolidinyl | N | CH | H | 3,4-diF-phenyl |
| Example 13 | morpholinyl | N | CH | H | 2-Cl-phenyl |

-continued
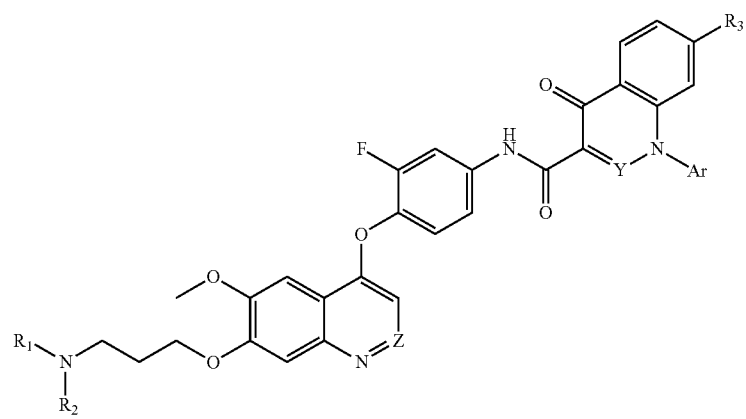
| Example | —NR₁R₂ | Y | Z | R₃ | Ar |
|---|---|---|---|---|---|
| Example 14 | 4-methylpiperidin-1-yl | N | CH | H | 2-fluorophenyl |
| Example 15 | 4-methylpiperidin-1-yl | N | CH | H | 2-chlorophenyl |
| Example 16 | pyrrolidin-1-yl | N | CH | H | 2-chlorophenyl |
| Example 17 | 4-methylpiperazin-1-yl | N | CH | H | 2-chlorophenyl |
| Example 18 | pyrrolidin-1-yl | N | CH | H | 2-bromo-4-fluorophenyl |
| Example 19 | 4-methylpiperazin-1-yl | N | CH | H | 2-bromo-4-fluorophenyl |

-continued
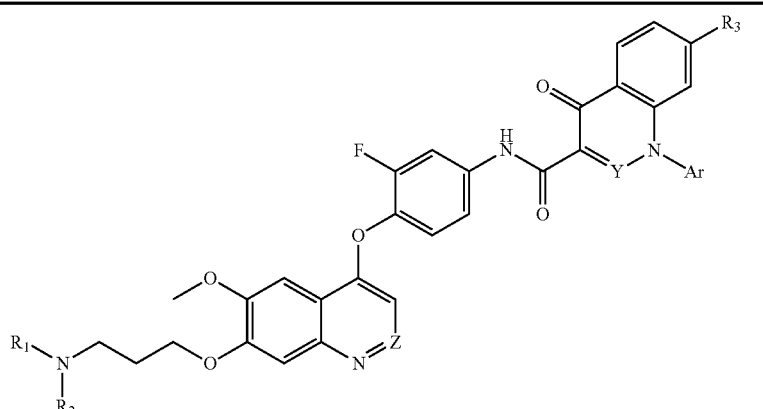
| Example | —NR₁R₂ | Y | Z | R₃ | Ar |
|---|---|---|---|---|---|
| Example 20 | piperidin-1-yl | N | CH | H | 2-Cl, 5-CF₃ phenyl |
| Example 21 | 4-methylpiperidin-1-yl | N | CH | H | 2-Cl, 5-CF₃ phenyl |
| Example 22 | pyrrolidin-1-yl | N | CH | H | 2-Cl, 5-CF₃ phenyl |
| Example 23 | 4-methylpiperazin-1-yl | N | CH | H | 2-Cl, 5-CF₃ phenyl |
| Example 24 | 4-methylpiperidin-1-yl | N | CH | H | 2,4-dimethylphenyl |
| Example 25 | pyrrolidin-1-yl | N | CH | H | 2,4-dimethylphenyl |
| Example 26 | 4-methylpiperazin-1-yl | N | CH | H | 2,4-dimethylphenyl |

-continued
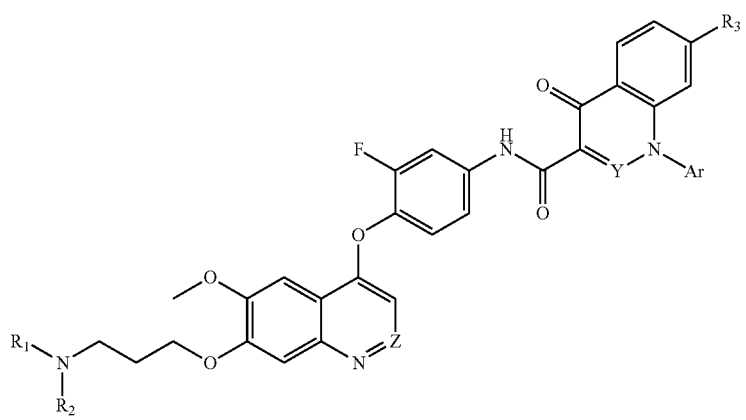
| Example | —NR₁R₂ | Y | Z | R₃ | Ar |
|---|---|---|---|---|---|
| Example 27 | piperidin-1-yl | N | CH | H | 2,4-dichlorophenyl |
| Example 28 | 4-methylpiperidin-1-yl | N | CH | H | 2,4-dichlorophenyl |
| Example 29 | piperidin-1-yl | N | CH | H | 2,6-dichlorophenyl |
| Example 30 | 4-methylpiperidin-1-yl | N | CH | H | 2,6-dichlorophenyl |
| Example 31 | pyrrolidin-1-yl | N | CH | H | 2,6-dichlorophenyl |
| Example 32 | 4-methylpiperazin-1-yl | N | CH | H | 2,6-dichlorophenyl |

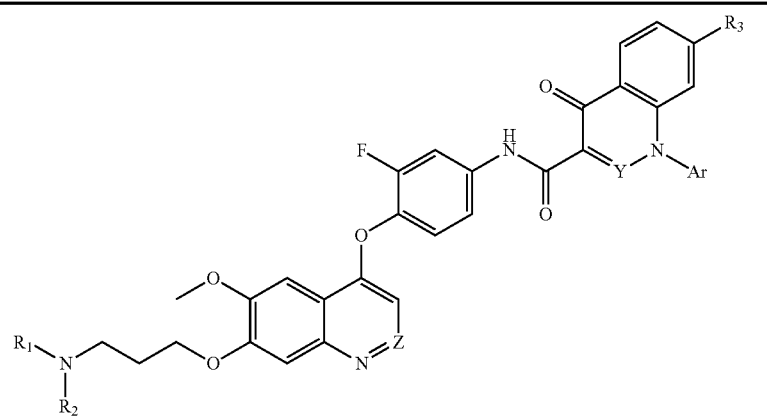
| Example | —NR₁R₂ | Y | Z | R₃ | Ar |
|---|---|---|---|---|---|
| Example 33 | 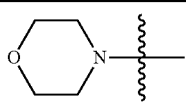 | N | CH | H | 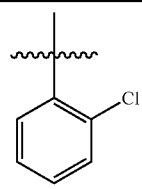 |
| Example 34 | 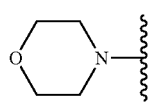 | N | CH | H | 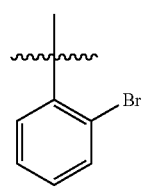 [SMILES: *c1ccccc1Br] |
| Example 35 | 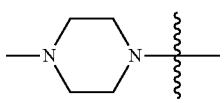 | N | CH | H | 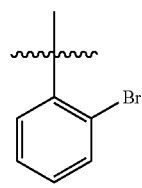 [SMILES: *c1ccccc1Br] |
| Example 36 | 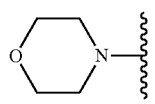 | N | CH | H | 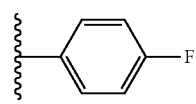 [SMILES: *c1ccc(F)cc1] |
| Example 37 | 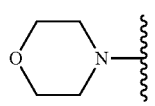 | N | CH | H | 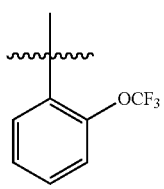 [SMILES: *c1ccccc1OC(F)(F)F] |
| Example 38 | 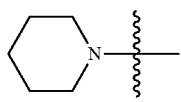 | N | CH | H | 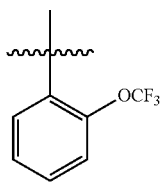 |
| Example 39 | 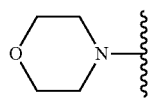 | N | CH | H | 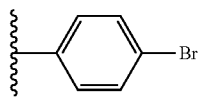 |

-continued
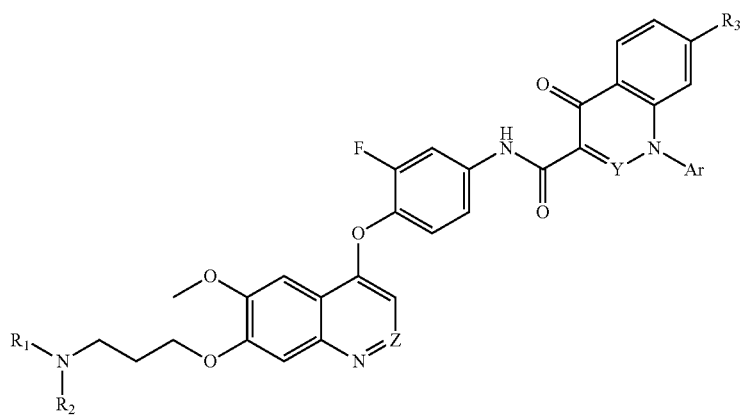
| Example | —NR₁R₂ | Y | Z | R₃ | Ar |
|---|---|---|---|---|---|
| Example 40 | N-methylpiperazinyl | N | CH | H | 4-Br-phenyl |
| Example 41 | pyrrolidinyl | N | CH | H | 2-F-phenyl |
| Example 42 | N-methylpiperazinyl | N | CH | H | 4-F-phenyl |
| Example 43 | N-methylpiperazinyl | N | CH | H | 2,4-diCl-phenyl |
| Example 44 | N-methylpiperazinyl | N | CH | F | 2-CF₃-phenyl |
| Example 45 | morpholinyl | N | CH | F | 2-F-phenyl |
| Example 46 | N-methylpiperazinyl | H | CH | H | 4-F-phenyl |

-continued
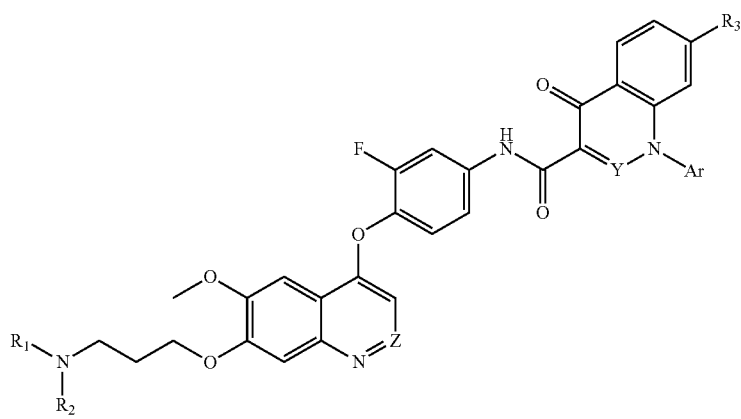
| Example | —NR₁R₂ | Y | Z | R₃ | Ar |
|---|---|---|---|---|---|
| Example 47 | 4-methylpiperidin-1-yl | H | CH | H | 2-fluorophenyl |
| Example 48 | morpholin-4-yl | H | CH | H | 2-(trifluoromethyl)phenyl |
| Example 49 | pyrrolidin-1-yl | H | CH | H | 4-fluorophenyl |
| Example 50 | piperidin-1-yl | H | CH | H | 2-fluorophenyl |
| Example 51 | pyrrolidin-1-yl | H | CH | H | 2-fluorophenyl |
| Example 52 | 4-methylpiperazin-1-yl | H | CH | H | 2-fluorophenyl |

-continued
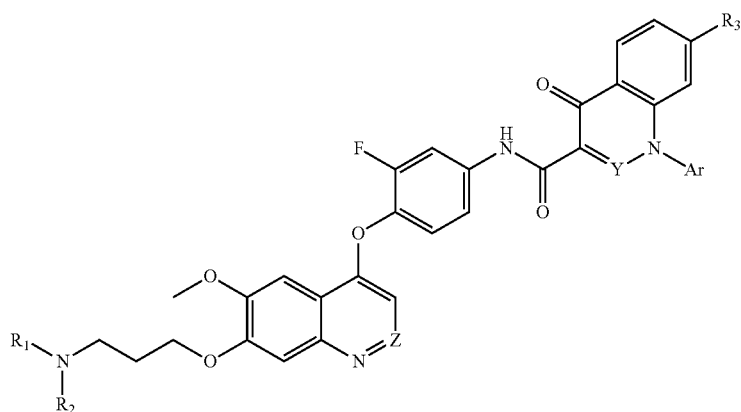
| Example | —NR₁R₂ | Y | Z | R₃ | Ar |
|---|---|---|---|---|---|
| Example 53 | piperidin-1-yl | H | CH | H | 2-chlorophenyl |
| Example 54 | 4-methylpiperidin-1-yl | H | CH | H | 2-chlorophenyl |
| Example 55 | 2-(pyrrolidin-1-yl)prop-2-yl | H | CH | H | 2-chlorophenyl |
| Example 56 | 4-methylpiperazin-1-yl | H | CH | H | 4-chlorophenyl |
| Example 57 | 4-methylpiperidin-1-yl | H | CH | H | 2-(trifluoromethyl)phenyl |
| Example 58 | 4-methylpiperidin-1-yl | H | CH | H | 3,4-difluorophenyl |

-continued
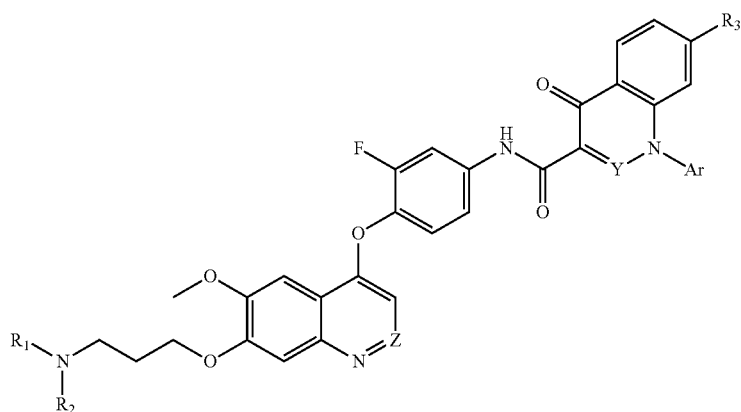
| Example | —NR₁R₂ | Y | Z | R₃ | Ar |
|---|---|---|---|---|---|
| Example 59 | piperidinyl | H | CH | H | 2-CF₃-phenyl |
| Example 60 | piperidinyl | H | CH | H | 3,4-difluorophenyl |
| Example 61 | piperidinyl | N | N | H | 2-F-phenyl |
| Example 62 | 4-methylpiperazinyl | N | N | H | 3-F-phenyl |
| Example 63 | pyrrolidinyl | N | N | H | 2-F-phenyl |
| Example 64 | piperidinyl | N | N | H | 3-F-phenyl |

-continued

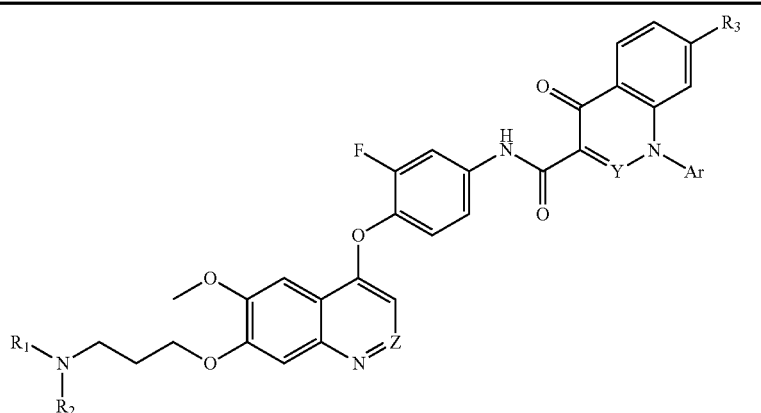

| Example | —NR₁R₂ | Y | Z | R₃ | Ar |
|---|---|---|---|---|---|
| Example 65 | piperidin-1-yl | N | N | H | 4-Br-phenyl |
| Example 66 | morpholin-4-yl | N | N | H | 4-Cl-phenyl |
| Example 67 | 4-methylpiperidin-1-yl | N | N | H | 4-Cl-phenyl |
| Example 68 | morpholin-4-yl | N | N | H | 2-F-4-Br-phenyl |
| Example 69 | 4-methylpiperazin-1-yl | N | N | H | 4-F-phenyl |
| Example 70 | pyrrolidin-1-yl | N | N | H | 2,4-di-Cl-phenyl |

Example No. 1

N-(3-fluoro-4-((6-methoxy-7-(3-(pyrrolidin-1-yl)propoxy)quinolin-4-yl)oxy)phenyl)-1-(2-(trifluoromethyl)phenyl)-4-oxo-1,4-dihydrocinnoline-3-carboxamide dihydrochloride Step A 1-(4-(3-chloropropoxy)-3-methoxyphenyl)ethanone (Intermediate II)

A stirred solution of 1-(4-hydroxy-3-methoxyphenyl)ethanone (600 g, 3.61 mol, Purchased from Shanghai Bangcheng Chemical Co., Ltd.) and anhydrous potassium carbonate (698 g, 5.055 mol) in 2500 mL of N,N-dimethylformamide was added drop-wise with an N,N-dimethylformamide solution of 1-bromo-3-chloropropane (795.9 g, 1.4 mol) while maintaining the temperature below 25° C. Then the resulted mixture was kept at 25° C. for 10 h. After completion of the reaction, the precipitate was filtered and the filter cake was washed by a small amount of N,N-dimethylformamide. The filtrate was poured into ice water slowly with vigorous stirring. The precipitate was filtered, washed with water, and dried to give 827.2 g solid. Yield: 93.8%.

Step B 1-(4-(3-chloropropoxy)-5-methoxy-2-nitrophenyl)ethanone (Intermediate III)

To a solution of intermediate II (200 g, 0.82 mol) in dichloromethane (5 v/w, 1000 mL), fuming nitric acid (130 g, 2.06 mol) was added drop-wise at a rate to maintain the reaction temperature below −10° C. Upon the completion of addition, the mixture was stirred for 2 h at −10~−20° C. After completion of the reaction, the reaction mixture was poured slowly into ice water, and the organic layer was separated and washed with brine until the aqueous layer became neutral, then dried with anhydrous sodium sulphate. The solution was evaporated to give 210 g of yellow solid. Yield: 89%.

Step C (E)-1-(4-(3-chloropropoxy)-5-methoxy-2-nitrophenyl)-3-(dimethylamino)prop-2-en-1-one (Intermediate IV)

To 1000 mL of toluene (5 v/w) were added 0.695 mol of intermediate III (200 g) and the mixture was heated to 110° C. to intermediate III completely dissolved. Then 3.476 mol of N,N-dimethylformamide dimethyl acetal (414.2 g) was added, and the reaction was heated to reflux for 16 h. After completion of the reaction, the resulting precipitate from the cooled reaction mixture was filtered to obtain the target compound as a yellow powder (180 g). Yield: 75.8%.

Step D 7-(3-chloropropoxy)-6-methoxyquinolin-4(1H)-one (Intermediate V)

0.44 moL of (E)-1-(4-(3-Chloropropoxy)-5-methoxy-2-nitrophenyl)-3-(dimethylamino)prop-2-en-1-one (intermediate IV) (150 g) was dissolved in 1200 mL of glacial acetic acid (8 v/w), and the mixture was heated to 40° C. After intermediate IV was completely dissolve, 2.20 mol (123.1 g) Iron powder was added slowly, then the reaction mixture was heated to 80° C. with mechanical stirring for 2 h. After completion of the reaction, the reaction mixture was filtered immediately to remove iron powder. The filtrate was collected and cooled to precipitate solid, and then filtered to give yellow solid, which was dissolved in glacial acetic acid and the solution was stirred at 80° C. for 30 min then filtered immediately again. The filtrate was cooled to precipitate solid, filtered, and the filter cake was washed with water until the aqueous layer became neutral, dried to give solid 79 g. Yield: 65%.

Step E 6-methoxy-7-(3-(pyrrolidin-1-yl)propoxy)quinolin-4(1H)-one (Intermediate VI)

To 620 mL of acetonitrile were added 0.232 mol (62 g) of intermediate V, and 1.16 mol of pyrrolidine (82.46 g), then the reaction mixture was heated to reflux for 8 h. After completion of the reaction, most of the solvent was evaporated, the raffinate was put in cold trap to precipitated solid, then filtered and the filter cake was washed with ethyl acetate to give solid 66.74 g. Yield 95.3%.

Step F 4-chloro-6-methoxy-7-(3-(pyrrolidin-1-yl)propoxy)quinoline (Intermediate VII)

To 315 mL of acetonitrile (5 v/w) were added 0.198 mol (63 g) of intermediate VI, 315 ml of phosphorus oxychloride (5 v/w), then the reaction mixture was heated to 85° C., refluxed for 6 h. After completion of the reaction, the mixture was evaporated to give gray viscous solid, which was poured into plenty of ice water, adjusted to pH 10 with 10% solution of potassium hydroxide, extracted with methylene dichloride. The organic layer was collected and dried with anhydrous sodium sulfate, and evaporated in vacuo to give solid 58 g. Yield: 87.3%.

Step G 4-(2-fluoro-4-nitrophenoxy)-6-methoxy-7-(3-(pyrrolidin-1-yl)propoxy)quinoline (Intermediate VIII)

To 250 mL of anhydrous chlorobenzene (5 v/w) were added 0.234 mol (36.73 g) of 2-fluoro-4-nitrophenol. The reaction mixture was heated to 145° C. then added 0.2 mol (62.5 g) of intermediate VII. The reaction was kept at this temperature for 20 h. After completion of the reaction, the reaction mixture was evaporated in vacuo to give gray solid, which was dissolved with methylene dichloride and washed with saturated potassium carbonate solution. The organic layer was dried, evaporated and recrystallized with ethanol to give solid 49.26 g. Yield: 71.4%.

Step H 3-fluoro-4-((6-methoxy-7-(3-(pyrrolidin-1-yl)propoxy)quinolin-4-yl)oxy)aniline (M-1)

To 1210.5 mL of 90% ethanol (25 v/w) were added 1.1 mol (61.42 g) of Iron powder, 6 mL of hydrochloric acid, then the reaction mixture was heated to 80° C. with stirring and kept this temperature for 15 min. After that, the reaction mixture was added portionwise 0.11 mol (48.42 g) intermediate VIII, then refluxed for 2 h. After completion of the reaction, the reaction mixture was filtered without cooling. The filtrate was collected and evaporated to give yellow solid 43 g. Yield: 95%.

Step I 2-fluorobenzoyl chloride (Intermediate a)

To 100 mL of toluene were added 0.714 mol of 2-fluorobenzoic acid (100 g) then the mixture was heated to 50° C. and added 5.7 mol (414 mL) sulfoxide chloride. The reaction mixture was refluxed for 7 h. After completion of the reaction, sulfoxide chloride was evaporated to give 2-fluorobenzoyl chloride 79 g. Yield: 70%.

Step J 5-(2-fluorobenzoyl)-2,2-dimethyl-1,3-dioxane-4,6-dione (Intermediate b)

To 300 mL of dichloromethane were added 82.6 g (0.574 mol) of 2,2-dimethyl-1,3-dioxane-4,6-dione, 87.5 g (0.7172 mol) of N,N-dimethylpyridin-4-amine with stirring. The mixture was cooled to 0° C. with ice-water bath, then was added a solution of 100 g (0.631 mol) intermediate a in 200 mL of dichloromethane dropwise. Upon the completion of addition, the reaction mixture was stirring at 0-5° C. for 2 h, and room temperature for another 2 h. After completion of the reaction, the reaction liquid was washed with 10% hydrochloric acid and water, then dried and evaporated to give solid 80 g. Yield: 50%.

Step K

Ethyl 3-(2-fluorophenyl)-3-oxopropanoate (Intermediate c)

To a mixture of 400 mL of ethyl alcohol and 200 mL of toluene were added 80 g of intermediate b. The reaction mixture was refluxed for 10 h. After completion of the reaction, the solvent was distilled off under reduced pressure to give black liquid 50 g. Yield: 78%.

Step L (E)-3-(2-fluorophenyl)-3-oxo-2-(2-(2(trifluoromethyl)phenyl)hydrazono) propionate (Intermediate d)

To 50 mL of 20% hydrochloric acid were added 10 g (0.06 mol) of 2-(trifluoromethyl)aniline. The mixture was cooled to 0° C., and a cold solution of 8.54 g (0.123 mol) of sodium nitrite in 200 mL of water was added dropwise with the reaction temperature being kept 0-5° C., then the reaction was kept at this temperature for 30 min. This reaction liquid was to be used directly later. To 200 mL of ethyl alcohol was added 10.2 g (0.124 mol) of sodium acetate and 10 g (0.0476 mol) of intermediate c. The mixture was cooled to 0° C., then added the diazonium salt solution prepared above dropwise with the reaction temperature being kept at 0-5° C. After that, the reaction mixture was kept at this temperature for 1 h. After completion of the reaction, the reaction mixture was filtered. The filter cake was washed with water, dried to give yellow solid 12 g. Yield: 70%.

Step M 4-oxo-1-(2-(trifluoromethyl)phenyl)-1,4-dihydrocinnoline-3-carboxylate (Intermediate e)

To 120 mL of anhydrous ethanol were added 15 g (0.039 mol) of intermediate d and 6.5 g (0.047 mol) of anhydrous potassium carbonate, the reaction mixture was refluxed for 5 h. After completion of the reaction, the reaction mixture was cooled and filtered to remove potassium carbonate, the filter cake was washed with a small amount of ethanol. The filtrate was concentrated then poured into 50 mL of water, adjusted to pH 5-6 with 15% hydrochloric acid, and precipitated a large amount of solid. The mixture was filtered, and the filter cake was washed with water then dried to give solid 12 g. Yield: 80%.

Step N 4-oxo-1-(2-(trifluoromethyl)phenyl)-1,4-dihydrocinnoline-3-carboxylic acid (Intermediate f)

To 160 mL of alcohol were added 10 g (0.027 mol) of intermediate e, 50 ml of 10% aqueous sodium hydroxide was added dropwise then the reaction was kept at room temperature for 5 to 8 h. After completion of the reaction, The reaction mixture was concentrated and poured into water, then adjusted to pH 5-6 with 15% hydrochloric acid, the precipitated solid was filtered and dried to give Intermediate f 7 g. Yield: 75%.

Step O 4-oxo-1-(2-(trifluoromethyl)phenyl)-1,4-dihydrocinnoline-3-carbonyl chloride (Q-1)

To 80 mL of sulfoxide chloride was added 10 g (0.03 mol) of intermediate f. The reaction mixture was refluxed for 8 h. After completion of the reaction, the excess sulfoxide chloride was evaporated to give intermediate Q-1 18.5 g. Yield: 81%.

Step P

N-(3-fluoro-4-((6-methoxy-7-(3-(pyrrolidin-1-yl)propoxy)quinolin-4-yl)oxy)phenyl)-4-oxo-1-(2-(trifluoromethyl)phenyl)-1,4-dihydrocinnoline-3-carboxamide dihydrochloride

Example 1

To 10 mL of anhydrous dichloromethane was added 0.2 g (0.48 mmol) intermediate M-1, 0.58 mmol of intermediate Q-1, 0.07 g (0.58 mmol) N,N-diisopropylethylamine. The mixture was stirring at room temperature for 10 h. After completion of the reaction, the organic layer was washed with 5% aqueous solution of potassium carbonate and brine, dried with anhydrous magnesium sulfate and evaporated to give gray solid 0.28 g, which was dissolved in 10 mL of acetone. The solution was added drop-wise acetone saturated solution of hydrochloric acid (2 mL) under the ice bath and precipitated large amount of solid. Upon the completion of addition, the mixture was stirred for 0.5 h, and then filtered, the filter cake was washed with acetone, dried to give target compound N-(3-fluoro-4-((6-methoxy-7-(3-(pyrrolidin-1-yl)propoxy)quinolin-4-yl)oxy)phenyl)-4-oxo-1-(2-(trifluoromethyl)phenyl)-1,4-dihydrocinnoline-3-carboxamide dihydrochloride (example 1) 0.3 g. Yield: 83.2%.

ESI-MS [M+H] (m/z): 727.7; $^1$H NMR (300 MHz, DMSO) δ 11.84 (s, 1H), 8.85 (d, J=6.5 Hz, 1H), 8.38 (d, J=7.8 Hz, 1H), 8.20-8.04 (m, 3H), 8.04-7.95 (m, 2H), 7.94-7.83 (m, 2H), 7.80 (s, 1H), 7.77-7.61 (m, 3H), 7.06 (dd, J=10.4, 7.8 Hz, 2H), 4.38 (t, J=5.6 Hz, 2H), 4.05 (d, J=12.1 Hz, 3H), 3.66-3.52 (m, 4H), 3.06 (s, 2H), 2.36 (s, 2H), 1.99 (m, 4H).

According to the methods in example 1, substituted intermediate Q-1 can be obtained by four steps including diazotization using different-substituted phenyl amine and intermediate c, which reacts with different-substituted M-1 to give compounds 2-45.

Example 2

N-(3-fluoro-4-((6-methoxy-7-(3-(piperidin-1-yl)propoxy)quinolin-4-yl)oxy)phenyl)-1-(2-chlorophenyl)-4-oxo-1,4-dihydrocinnoline-3-carboxamide dihydrochloride ESI-MS [M+H] (m/z): 741.7; $^1$H NMR (300 MHz, DMSO) δ 11.84 (s, 1H), 8.83 (d, J=6.5 Hz, 1H), 8.40 (d, J=7.2 Hz, 1H), 8.13 (dd, J=12.8, 2.1 Hz, 1H), 7.97-7.86 (m, 3H), 7.85-7.78 (m, 3H), 7.78-7.70 (m, 3H), 7.65 (t, J=8.8 Hz, 1H), 7.10 (d, J=8.6 Hz, 1H), 7.02 (d, J=6.4 Hz, 1H), 4.37 (t, J=5.8 Hz, 2H), 4.07 (s, 3H), 3.50 (d, J=11.6 Hz, 4H), 2.92 (d, J=9.6 Hz, 2H), 2.38 (d, J=6.5 Hz, 2H), 1.81 (m, 6H).

Example 3

N-(3-fluoro-4-((6-methoxy-7-(3-(piperidin-1-yl)propoxy)quinolin-4-yl)oxy)phenyl)-1-(4-bromophenyl)-4-oxo-1,4-dihydrocinnoline-3-carboxamide dihydrochloride ESI-MS [M+H] (m/z): 752.6; $^1$H NMR (300 MHz, DMSO) δ 11.78 (s, 1H), 8.55 (s, 1H), 8.51-8.38 (m, 2H), 8.00

(d, J=12.1 Hz, 1H), 7.87-7.22 (m, 10H), 6.51 (s, 1H), 4.24 (s, 2H), 3.96 (s, 3H), 3.06 (s, 6H), 2.27 (s, 2H), 1.76 (s, 4H), 1.52 (s, 2H).

Example 4

N-(3-fluoro-4-((6-methoxy-7-(3-(morpholin-4-ylpropoxy)quinolin-4-yl)oxy)phenyl)-1-(2-(trifluoromethyl)phenyl)-4-oxo-1,4-dihydrocinnoline-3-carboxamide dihydrochloride ESI-MS [M+H] (m/z): 743.7; $^1$H NMR (300 MHz, DMSO) δ 11.69 (s, 1H), 8.48 (d, J=5.2 Hz, 1H), 8.39 (d, J=7.4 Hz, 4H), 8.15 (d, J=7.9 Hz, 1H), 8.03 (dt, J=16.3, 7.2 Hz, 1H), 8.22-7.82 (m, 3H), 7.88 (t, J=7.3 Hz, 1H), 7.70 (t, J=7.6 Hz, 1H), 7.62 (d, J=8.7 Hz, 1H), 7.07 (d, J=8.6 Hz, 1H), 6.50 (d, J=5.1 Hz, 1H), 4.21 (t, J=6.4 Hz, 2H), 3.96 (s, 3H), 3.65-3.51 (m, 4H), 2.57-2.25 (m, 6H), 2.00 (dd, J=13.7, 6.7 Hz, 2H).

Example 5

N-(3-fluoro-4-((6-methoxy-7-(3-(piperidin-1-yl)propoxy)quinolin-4-yl)oxy)phenyl)-1-(2-(trifluoromethyl)phenyl)-4-oxo-1,4-dihydrocinnoline-3-carboxamide dihydrochloride ESI-MS [M+H] (m/z): 759.7; $^1$H NMR (300 MHz, DMSO) δ 12.03-11.19 (m, 1H), 8.65-8.40 (m, 1H), 8.40-8.25 (m, 1H), 8.29-7.83 (m, 3H), 7.82-7.65 (m, 4H), 7.65-7.37 (m, 2H), 7.36-6.77 (m, 1H), 6.49 (d, J=1 Hz, 1H), 4.21 (t, J=6.2 Hz, 2H), 4.04-3.91 (m, 3H), 3.82 (s, 4H), 2.55 (dd, m, 10.5 Hz, 2H), 2.17-1.96 (m, 2H), 1.57 (d, J=4.8 Hz, 2H), 1.48-1.35 (m, 2H), 1.26 (dd, J=15.4, 8.5 Hz, 2H).

Example 6

N-(3-fluoro-4-((6-methoxy-7-(3-(piperidin-1-yl)propoxy)quinolin-4-yl)oxy)phenyl)-1-(3-(trifluoromethyl)phenyl)-4-oxo-1,4-dihydrocinnoline-3-carboxamide ESI-MS [M+H] (m/z): 759.7; $^1$H NMR (300 MHz, DMSO) δ 11.88 (s, 1H), 8.50 (d, J=5.0 Hz, 1H), 8.39 (d, J=7.7 Hz, 1H), 8.25 (s, 1H), 8.11-7.84 (m, 5H), 7.72-7.42 (m, 5H), 7.33 (d, J=8.8 Hz, 1H), 6.52 (d, J=5.0 Hz, 1H), 4.27 (s, 2H), 3.97 (s, 3H), 3.18 (s, 4H), 2.30 (s, 2H), 1.80 (s, 4H), 1.55 (s, 2H), 1.23 (s, 2H).

Example 7

N-(3-fluoro-4-((6-methoxy-7-(3-(piperidin-1-yl)propoxy)quinolin-4-yl)oxy)phenyl)-1-(2-fluorophenyl)-4-oxo-1,4-dihydrocinnoline-3-carboxamide ESI-MS [M+H] (m/z): 759.7; $^1$H NMR (300 MHz, DMSO) δ 11.78 (s, 1H), 8.82 (d, J=6.5 Hz, 1H), 8.37 (d, J=7.4 Hz, 1H), 8.19-7.93 (m, 5H), 7.92-7.76 (m, 3H), 7.66 (t, m, 3H), 7.06 (d, J=8.7 Hz, 3H), 7.00 (d, J=6.4 Hz, 1H), 4.36 (d, J=5.2 Hz, 2H), 4.05 (s, 3H), 3.48 (d, J=11.4 Hz, 4H), 2.50-2.44 (m, 6H), 2.38 (s, 2H), 1.81 (s, 2H).

Example 8

N-(3-fluoro-4-((6-methoxy-7-(3-(4-methylpiperazin-1-yl)propoxy)quinolin-4-yl)oxy)phenyl)-1-(2-(trifluoromethyl)phenyl)-4-oxo-1,4-dihydrocinnoline-3-carboxamide ESI-MS [M+H] (m/z): 774.7; $^1$H NMR (300 MHz, DMSO) δ 11.79 (s, 1H), 8.83 (d, J=6.5 Hz, 1H), 8.38 (d, J=7.6 Hz, 1H), 8.18-8.04 (m, 3H), 7.99 (t, J=7.1 Hz, 2H), 7.94-7.78 (m, 3H), 7.68 (m, 8.6 Hz, 3H), 7.07 (d, J=8.7 Hz, 1H), 7.02 (d, J=6.4 Hz, 1H), 4.37 (d, J=5.9 Hz, 2H), 4.07 (s, 3H), 3.44 (m, 10H), 2.85 (s, 3H), 2.39 (s, 2H).

Example 9

N-(3-fluoro-4-((6-methoxy-7-(3-(piperidin-1-yl)propoxy)quinolin-4-yl)oxy)phenyl)-1-(3-fluorophenyl)-4-oxo-1,4-dihydrocinnoline-3-carboxamide ESI-MS [M+H] (m/z): 691.7; $^1$H NMR (300 MHz, DMSO) δ 11.88 (s, 1H), 8.72 (d, J=6.5 Hz, 1H), 8.47 (d, J=7.4 Hz, 1H), 8.29-8.03 (m, 5H), 8.02-7.86 (m, 3H), 7.76 (dt, m, 3H), 7.16 (d, J=8.7 Hz, 3H), 7.08 (d, J=6.4 Hz, 1H), 4.38 (d, J=5.2 Hz, 2H), 4.15 (s, 3H), 3.48 (d, J=11.4 Hz, 4H), 2.50-2.44 (m, 6H), 2.38 (s, 2H), 1.81 (s, 2H).

Example 10

N-(3-fluoro-4-((6-methoxy-7-(3-(piperidin-1-yl)propoxy)quinolin-4-yl)oxy)phenyl)-1-(4-chlorophenyl)-4-oxo-1,4-dihydrocinnoline-3-carboxamide ESI-MS [M+H] (m/z): 708.1; $^1$H NMR (300 MHz, DMSO) δ 11.78 (s, 1H), 8.66 (s, 1H), 8.52-8.38 (m, 2H), 8.00 (d, J=12.1 Hz, 1H), 7.87-7.22 (m, 10H), 6.51 (s, 1H), 4.21 (s, 2H), 3.94 (s, 3H), 3.05 (s, 6H), 2.26 (s, 2H), 1.86 (s, 4H), 1.52 (s, 2H).

Example 11

N-(3-fluoro-4-((6-methoxy-7-(3-(piperidin-1-yl)propoxy)quinolin-4-yl)oxy)phenyl)-1-(3,4-difluorophenyl)-4-oxo-1,4-dihydrocinnoline-3-carboxamide ESI-MS [M+H] (m/z): 710.1; $^1$H NMR (300 MHz, DMSO) δ 11.69 (s, 1H), 8.48 (d, J=5.2 Hz, 1H), 8.37 (d, J=7.4 Hz, 4H), 8.14 (d, J=7.9 Hz, 1H), 8.01 (dt, J=16.3, 7.2 Hz, 1H), 8.22-7.85 (m, 3H), 7.87 (t, J=7.3 Hz, 1H), 7.72 (t, J=7.6 Hz, 1H), 7.64 (d, J=8.7 Hz, 1H), 7.06 (d, J=8.6 Hz, 1H), 6.52 (d, J=5.1 Hz, 1H), 4.21 (t, J=6.4 Hz, 2H), 3.96 (s, 3H), 3.65-3.50 (m, 4H), 2.57-2.25 (m, 6H), 2.00 (dd, J=13.7, 6.7 Hz, 2H).

Example 12

N-(3-fluoro-4-((6-methoxy-7-(3-(pyrrolidin-1-yl)propoxy)quinolin-4-yl)oxy)phenyl)-1-(3,4-difluorophenyl)-4-oxo-1,4-dihydrocinnoline-3-carboxamide ESI-MS [M+H] (m/z): 705.7; $^1$H NMR (300 MHz, DMSO) δ 11.79 (s, 1H), 8.85 (d, J=6.5 Hz, 1H), 8.40 (d, J=7.6 Hz, 1H), 8.17-8.04 (m, 3H), 7.98 (t, J=7.1 Hz, 2H), 7.94-7.78 (m, 3H), 7.68 (m, 3H), 7.08 (d, J=8.7 Hz, 1H), 7.04 (d, J=6.4 Hz, 1H), 4.37 (d, J=5.9 Hz, 2H), 4.07 (s, 3H), 3.44 (m, 11H), 2.61 (s, 3H), 2.39 (s, 2H).

Example 13

N-(3-fluoro-4-((6-methoxy-7-(3-(4-methylpiperidin-1-yl)propoxy)quinolin-4-yl)oxy)phenyl)-1-(4-fluorophenyl)-4-oxo-1,4-dihydrocinnoline-3-carboxamide ESI-MS [M+H] (m/z): 722.2; $^1$H NMR (300 MHz, DMSO) δ 11.78 (s, 1H), 8.86 (d, J=6.5 Hz, 1H), 8.39 (d, J=7.6

Hz, 1H), 8.17-8.04 (m, 3H), 7.99 (t, J=7.1 Hz, 2H), 7.93-7.78 (m, 3H), 7.68 (m, 8.6 Hz, 3H), 7.08 (d, J=8.7 Hz, 1H), 7.04 (d, J=6.4 Hz, 1H), 4.36 (d, J=5.9 Hz, 2H), 4.08 (s, 3H), 3.43 (m, 11H), 2.60 (s, 3H), 2.39 (s, 2H).

Example 14

N-(3-fluoro-4-((6-methoxy-7-(3-(4-methylpiperidin-1-yl)propoxy)quinolin-4-yl)oxy)phenyl)-1-(2-fluorophenyl)-4-oxo-1,4-dihydrocinnoline-3-carboxamide ESI-MS [M+H] (m/z): 694.1; $^1$H NMR (300 MHz, DMSO) δ 11.83 (s, 1H), 8.86 (d, J=6.5 Hz, 1H), 8.39 (d, J=7.8 Hz, 1H), 8.21-8.04 (m, 3H), 8.04-7.96 (m, 2H), 7.95-7.83 (m, 2H), 7.80 (s, 1H), 7.78-7.61 (m, 3H), 7.06 (dd, J=10.4, 7.8 Hz, 2H), 4.37 (t, J=5.6 Hz, 2H), 4.06 (d, J=12.1 Hz, 3H), 3.66-3.51 (m, 4H), 3.04 (s, 2H), 2.40 (s, 2H), 1.98 (m, 4H).

Example 15

N-(3-fluoro-4-((6-methoxy-7-(3-(4-methylpiperidin-1-yl)propoxy)quinolin-4-yl)oxy)phenyl)-1-(2-chlorophenyl)-4-oxo-1,4-dihydrocinnoline-3-carboxamide dihydrochloride ESI-MS [M+H] (m/z): 723.1; $^1$H NMR (300 MHz, DMSO) δ 11.77 (s, 1H), 8.84 (d, J=6.5 Hz, 1H), 8.38 (d, J=7.6 Hz, 1H), 8.18-8.06 (m, 3H), 7.98 (t, J=7.1 Hz, 2H), 7.94-7.79 (m, 3H), 7.69 (m, 3H), 7.06 (d, J=8.7 Hz, 1H), 7.02 (d, J=6.4 Hz, 1H), 4.38 (d, J=5.9 Hz, 2H), 4.06 (s, 3H), 3.46 (m, 10H), 2.86 (s, 3H), 2.38 (s, 2H).

Example 16

N-(3-fluoro-4-((6-methoxy-7-(3-(pyrrolidin-1-yl)propoxy)quinolin-4-yl)oxy)phenyl)-1-(2-chlorophenyl)-4-oxo-1,4-dihydrocinnoline-3-carboxamide dihydrochloride ESI-MS [M+H] (m/z): 709.7.

Example 17

N-(3-fluoro-4-((6-methoxy-7-(3-(4-methylpiperazin-1-yl)propoxy)quinolin-4-yl)oxy)phenyl)-1-(2-chlorophenyl)-4-oxo-1,4-dihydrocinnoline-3-carboxamide dihydrochloride ESI-MS [M+H] (m/z): 695.6.

Example 18

N-(3-fluoro-4-((6-methoxy-7-(3-(pyrrolidin-1-yl)propoxy)quinolin-4-yl)oxy)phenyl)-1-(2-bromo-4-fluorophenyl)-4-oxo-1,4-dihydrocinnoline-3-carboxamide ESI-MS [M+H] (m/z): 756.5

Example 19

N-(3-fluoro-4-((6-methoxy-7-(3-(4-methylpiperazin-1-yl)propoxy)quinolin-4-yl)oxy)phenyl)-1-(2-bromo-4-fluorophenyl)-4-oxo-1,4-dihydrocinnoline-3-carboxamide ESI-MS [M+H] (m/z): 785.6.

Example 20

N-(3-fluoro-4-((6-methoxy-7-(3-(piperidin-1-yl)propoxy)quinolin-4-yl)oxy)phenyl)-1-(2-chloro-5-(trifluoromethyl)phenyl)-4-oxo-1,4-dihydrocinnoline-3-carboxamide ESI-MS [M+H] (m/z): 776.1.

Example 21

N-(3-fluoro-4-((6-methoxy-7-(3-(4-methylpiperidin-1-yl)propoxy)quinolin-4-yl)oxy)phenyl)-1-(2-chloro-5-(trifluoromethyl)phenyl)-4-oxo-1,4-dihydrocinnoline-3-carboxamide ESI-MS [M+H] (m/z): 790.2.

Example 22

N-(3-fluoro-4-((6-methoxy-7-(3-(pyrrolidin-1-yl)propoxy)quinolin-4-yl)oxy)phenyl)-1-(2-chloro-5-(trifluoromethyl)phenyl)-4-oxo-1,4-dihydrocinnoline-3-carboxamide ESI-MS [M+H] (m/z): 762.1.

Example 23

N-(3-fluoro-4-((6-methoxy-7-(3-(4-methylpiperazin-1-yl)propoxy)quinolin-4-yl)oxy)phenyl)-1-(2-chloro-5-(trifluoromethyl)phenyl)-4-oxo-1,4-dihydrocinnoline-3-carboxamide ESI-MS [M+H] (m/z): 791.1.

Example 24

N-(3-fluoro-4-((6-methoxy-7-(3-(4-methylpiperidin-1-yl)propoxy)quinolin-4-yl)oxy)phenyl)-1-(2,4-dimethylphenyl)-4-oxo-1,4-dihydrocinnoline-3-carboxamide ESI-MS [M+H] (m/z): 715.8.

Example 25

N-(3-fluoro-4-((6-methoxy-7-(3-(pyrrolidin-1-yl)propoxy)quinolin-4-yl)oxy)phenyl)-1-(2,4-dimethylphenyl)-4-oxo-1,4-dihydrocinnoline-3-carboxamide ESI-MS [M+H] (m/z): 687.6.

Example 26

N-(3-fluoro-4-((6-methoxy-7-(3-(4-methylpiperazin-1-yl)propoxy)quinolin-4-yl)oxy)phenyl)-1-(2,4-dimethylphenyl)-4-oxo-1,4-dihydrocinnoline-3-carboxamide ESI-MS [M+H] (m/z): 716.8.

Example 27

N-(3-fluoro-4-((6-methoxy-7-(3-(piperidin-1-yl)propoxy)quinolin-4-yl)oxy)phenyl)-1-(2,4-dichlorophenyl)-4-oxo-1,4-dihydrocinnoline-3-carboxamide ESI-MS [M+H] (m/z): 742.6

Example 28

N-(3-fluoro-4-((6-methoxy-7-(3-(4-methylpiperidin-1-yl)propoxy)quinolin-4-yl)oxy)phenyl)-1-(2,4-dichlorophenyl)-4-oxo-1,4-dihydrocinnoline-3-carboxamide ESI-MS [M+H] (m/z): 756.6.

Example 29

N-(3-fluoro-4-((6-methoxy-7-(3-(piperidin-1-yl)propoxy)quinolin-4-yl)oxy)phenyl)-1-(2,6-dichlorophenyl)-4-oxo-1,4-dihydrocinnoline-3-carboxamide ESI-MS [M+H] (m/z): 742.6.

Example 30

N-(3-fluoro-4-((6-methoxy-7-(3-(4-methylpiperidin-1-yl)propoxy)quinolin-4-yl)oxy)phenyl)-1-(2,6-dichlorophenyl)-4-oxo-1,4-dihydrocinnoline-3-carboxamide ESI-MS [M+H] (m/z): 756.6.

Example 31

N-(3-fluoro-4-((6-methoxy-7-(3-(pyrrolidin-1-yl)propoxy)quinolin-4-yl)oxy)phenyl)-1-(2,6-dichlorophenyl)-4-oxo-1,4-dihydrocinnoline-3-carboxamide ESI-MS [M+H] (m/z): 728.3.

Example 32

N-(3-fluoro-4-((6-methoxy-7-(3-(4-methylpiperazin-1-yl)propoxy)quinolin-4-yl)oxy)phenyl)-1-(2,6-dichlorophenyl)-4-oxo-1,4-dihydrocinnoline-3-carboxamide ESI-MS [M+H] (m/z): 757.6.

Example 33

N-(3-fluoro-4-((6-methoxy-7-(3-(morpholin-4-yl)propoxy)quinolin-4-yl)oxy)phenyl)-1-(2-chlorophenyl)-4-oxo-1,4-dihydrocinnoline-3-carboxamide ESI-MS [M+H] (m/z): 710.1.

Example 34

N-(3-fluoro-4-((6-methoxy-7-(3-(morpholin-4-yl)propoxy)quinolin-4-yl)oxy)phenyl)-1-(2-bromophenyl)-4-oxo-1,4-dihydrocinnoline-3-carboxamide ESI-MS [M+H] (m/z): 754.6.

Example 35

N-(3-fluoro-4-((6-methoxy-7-(3-(4-methylpiperazin-1-yl)propoxy)quinolin-4-yl)oxy)phenyl)-1-(2-bromophenyl)-4-oxo-1,4-dihydrocinnoline-3-carboxamide ESI-MS [M+H] (m/z): 767.6.

Example 36

N-(3-fluoro-4-((6-methoxy-7-(3-(morpholin-4-yl)propoxy)quinolin-4-yl)oxy)phenyl)-1-(4-fluorophenyl)-4-oxo-1,4-dihydrocinnoline-3-carboxamide ESI-MS [M+H] (m/z): 693.7.

Example 37

N-(3-fluoro-4-((6-methoxy-7-(3-(morpholin-4-yl)propoxy)quinolin-4-yl)oxy)phenyl)-1-(2-(trifluoromethoxy)phenyl)-4-oxo-1,4-dihydrocinnoline-3-carboxamide ESI-MS [M+H] (m/z): 759.7.

Example 38

N-(3-fluoro-4-((6-methoxy-7-(3-(piperidin-1-yl)propoxy)quinolin-4-yl)oxy)phenyl)-1-(2-(trifluoromethoxy)phenyl)-4-oxo-1,4-dihydrocinnoline-3-carboxamide ESI-MS [M+H] (m/z): 757.7.

Example 39

N-(3-fluoro-4-((6-methoxy-7-(3-(morpholin-4-yl)propoxy)quinolin-4-yl)oxy)phenyl)-1-(4-bromophenyl)-4-oxo-1,4-dihydrocinnoline-3-carboxamide ESI-MS [M+H] (m/z): 754.6.

Example 40

N-(3-fluoro-4-((6-methoxy-7-(3-(4-methylpiperazin-1-yl)propoxy)quinolin-4-yl)oxy)phenyl)-1-(4-bromophenyl)-4-oxo-1,4-dihydrocinnoline-3-carboxamide ESI-MS [M+H] (m/z): 706.7.

Example 41

N-(3-fluoro-4-((6-methoxy-7-(3-(pyrrolidin-1-yl)propoxy)quinolin-4-yl)oxy)phenyl)-1-(2-fluorophenyl)-4-oxo-1,4-dihydrocinnoline-3-carboxamide ESI-MS [M+H] (m/z): 677.7.

Example 42

N-(3-fluoro-4-((6-methoxy-7-(3-(4-methylpiperazin-1-yl)propoxy)quinolin-4-yl)oxy)phenyl)-1-(4-fluorophenyl)-4-oxo-1,4-dihydrocinnoline-3-carboxamide ESI-MS [M+H] (m/z): 706.7.

Example 43

N-(3-fluoro-4-((6-methoxy-7-(3-(4-methylpiperazin-1-yl)propoxy)quinolin-4-yl)oxy)phenyl)-1-(2,4-dichlorophenyl)-4-oxo-1,4-dihydrocinnoline-3-carboxamide ESI-MS [M+H] (m/z): 757.6.

Example 44

N-(3-fluoro-4-((6-methoxy-7-(3-(4-methylpiperazin-1-yl)propoxy)quinolin-4-yl)oxy)phenyl)-1-(2-(trifluoromethyl)phenyl)-4-oxo-1,4-dihydrocinnoline-3-carboxamide ESI-MS [M+H] (m/z): 774.7.

Example 45

N-(3-fluoro-4-((6-methoxy-7-(3-(morpholin-4-yl)propoxy)quinolin-4-yl)oxy)phenyl)-1-(2-fluorophenyl)-4-oxo-1,4-dihydrocinnoline-3-carboxamide ESI-MS [M+H] (m/z): 711.6.

Example 46

N-(3-fluoro-4-((6-methoxy-7-(3-(morpholin-4-yl)propoxy)quinolin-4-yl)oxy)phenyl)-1-(2-fluorophenyl)-4-oxo-1,4-dihydroquinolin-3-carboxamide dihydrochloride

Step Q

E)-3-(dimethylamino)-2-(2-fluorobenzoyl)acrylate (g)

A mixture of intermediate c (19 g, 0.08 mol), and DMF-DMA (0.64 mol, 97 ml), was heated to 50° C. kept at this temperature for 4 h. After completion of the reaction, the solvent was evaporated in vacuo, to give brown oil 18.8 g, 80% Yield.

Step R (E)-ethyl-2-(2-fluorobenzoyl)-3-((4-fluorophenyl)amino)acrylate(h)

To 35 mL of toluene (5 v/w) were added intermediate g (7 g, 0.025 mol), 4-fluoroaniline (1.2 g, 0.030 mol), the reaction mixture was stirred under reflux for 10 h. After completion of the reaction, the solvent was evaporated in vacuo to give yellow oil, which was stirred in anhydrou ether for 0.5 h, the precipitate was filtered, dried to obtain white solid 6.5 g. Yield: 70%.

Step S 1-(4-fluorophenyl)-4-oxo-1,4-dihydroquinoline-3-carboxylate (j)

To 120 mL of anhydrous ethylalcohol (8 v/w) were added intermediate h (14 g, 0.039 mol) and potassium carbonate (6.5 g, 0.047 mol), the mixture was stirred at room temperature for 5 h, After completion of the reaction, the reaction mixture was filtered, and the filter cake was washed with a small amount of ethylalcohol, then the filtrate was concentrated and poured into water and adjusted to pH 5-6 with 6 N HCl. The precipitate was filtered, washed with water, and dried to obtain solid 11 g. Yield: 80%.

Step T 1-(4-fluorophenyl)-4-oxo-1,4-dihydroquinoline-3-carboxylic acid (k)

To a solution of intermediate j (5 g, 0.013 mol) dissolved in ethylalcohol (50 ml, 10 v/w) was added 1N NaOH aq (100 ml). The mixture was stirred at room temperature for 3 h. After completion of the reaction, the solvent was evaporated in vacuo, and the residue was poured into water (50 ml) and extracted with CH2Cl2 (150 mL*4). Then the aqueous layer was separated and acidified to pH 6 with 6N aqueous hydrochloric acid, then stirred at room temperature for 0.5 h, and the precipitate was filtered to give white solid 2.8 g. Yield: 60%.

Step U 1-(4-fluorophenyl)-4-oxo-1,4-dihydroquinoline-3-carbonyl chloride (Q-2)

A mixture of intermediate k 2 g (0.007 moL) and sulfoxide chloride (20 mL) was heated to reflux for 6 h, the excess sulfoxide chloride was evaporated in vacuo to obtain white solid 2 g. Yield: 95.1%.

Step V

N-(3-fluoro-4-((6-methoxy-7-(3-(4-methyl-piperazin-1-yl)propoxy)quinolin-4-yl)oxy)phenyl)-4-oxo-1-(4-fluorophenyl)-1,4-dihydroquinoline-3-carboxamide dihydrochloride (Example 46)

A mixture of intermediate M-1 (0.2 g, 0.48 mmol), intermediate Q-2 (0.58 mmol) dissolved in anhydrous $CH_2Cl_2$ (10 mL), N,N-diisopropylethylamine (0.07 g, 0.58 mmol) was stirred at room temperature for 10 h. After the reaction is complete, the dichloromethane layer was washed with 5% aqueous solution of $K_2CO_3$, brine in sequence, dried with anhydrous magnesium sulfate. The solvent was evaporated in vacuo to obtain gray solid 0.26 g, which was dissolved in acetone (10 mL), and to the mixture was added drop-wise acetone saturated solution of hydrochloric acid (2 mL) under the ice bath. Upon the completion of addition, the resulting precipitate was stirred for 0.5 h, and then filtered, washed with acetone, dried to give target compound 0.26 g. Yield: 80%.

ESI-MS [M+H] (m/z): 705.7; $^1$H NMR (300 MHz, DMSO) δ 10.71 (s, 1H), 8.77 (s, 1H), 8.54 (d, J=5.2 Hz, 1H), 7.78 (d, J=4.8 Hz, 5H), 7.67-7.41 (m, 7H), 7.23 (s, 2H), 6.65 (d, J=4.8 Hz, 1H), 4.38 (d, J=5.9 Hz, 2H), 4.06 (s, 3H), 3.46-2.94 (m, 10H), 2.86 (s, 3H), 2.38 (s, 2H).

According to the methods in example 46, substituted intermediate Q-2 can be obtained by reaction using intermediate c and DMF-DMA, followed by four steps with substituted phenyl amine, which reacts with substituted M-1 to give compound 47-60.

Example 47

N-(3-fluoro-4-((6-methoxy-7-(3-(4-methylpiperidin-1-yl)propoxy)quinolin-4-yl)oxy)phenyl)-1-(2-fluorophenyl)-4-oxo-1,4-dihydroquinoline-3-carboxamide ESI-MS [M+H] (m/z): 704.7; $^1$H NMR (300 MHz, DMSO) δ 11.11 (s, 1H), 8.66 (s, 1H), 8.53 (d, J=5.2 Hz, 1H), 7.80 (d, J=4.8 Hz, 5H), 7.67-7.41 (m, 7H), 7.23 (s, 2H), 6.68 (d, J=4.8 Hz, 1H), 4.33 (d, J=5.9 Hz, 2H), 4.06 (s, 3H), 3.43-3.14 (m, 11H), 2.60 (s, 3H), 2.39 (s, 2H).

Example 48

N-(3-fluoro-4-((6-methoxy-7-(3-(morpholin-4-yl)propoxy)quinolin-4-yl)oxy)phenyl)-4-oxo-1-(2-(trifluoromethyl)phenyl)-1,4-dihydroquinoline-3-carboxamide dihydrochloride ESI-MS [M+H] (m/z): 742.7; $^1$H NMR (300 MHz, DMSO) δ 10.89 (s, 1H), 8.72 (s, 1H), 8.55 (d, J=5.2 Hz, 1H), 7.79 (d, J=4.8 Hz, 5H), 7.63-7.39 (m, 7H), 7.25 (s, 2H), 6.69 (d, J=4.8 Hz, 1H), 4.21 (t, J=6.4 Hz, 2H), 3.96 (s, 3H), 3.65-3.50 (m, 4H), 2.57-2.25 (m, 6H), 2.00 (dd, J=13.7, 6.7 Hz, 2H).

Example 49

N-(3-fluoro-4-((6-methoxy-7-(3-(piperidin-1-yl)propoxy)quinolin-4-yl)oxy)phenyl)-1-(4-fluorophenyl)-4-oxo-1,4-dihydroquinoline-3-carboxamide dihydrochloride ESI-MS [M+H] (m/z): 676.7.

Example 50

N-(3-fluoro-4-((6-methoxy-7-(3-(piperidin-1-yl)propoxy)quinolin-4-yl)oxy)phenyl)-1-(2-fluorophenyl)-4-oxo-1,4-dihydroquinoline-3-carboxamide ESI-MS [M+H] (m/z): 690.7.

Example 51

N-(3-fluoro-4-((6-methoxy-7-(3-(pyrrolidin-1-yl)propoxy)quinolin-4-yl)oxy)phenyl)-1-(2-fluorophenyl)-4-oxo-1,4-dihydroquinoline-3-carboxamide ESI-MS [M+H] (m/z): 676.7.

Example 52

N-(3-fluoro-4-((6-methoxy-7-(3-(4-methylpiperazin-1-yl)propoxy)quinolin-4-yl)oxy)phenyl)-1-(2-fluorophenyl)-4-oxo-1,4-dihydroquinoline-3-carboxamide ESI-MS [M+H] (m/z): 705.7.

Example 53

N-(3-fluoro-4-((6-methoxy-7-(3-(piperidin-1-yl)propoxy)quinolin-4-yl)oxy)phenyl)-1-(2-chlorophenyl)-4-oxo-1,4-dihydroquinoline-3-carboxamide ESI-MS [M+H] (m/z): 707.1.

Example 54

N-(3-fluoro-4-((6-methoxy-7-(3-(4-methylpiperidin-1-yl)propoxy)quinolin-4-yl)oxy)phenyl)-1-(2-chlorophenyl)-4-oxo-1,4-dihydroquinoline-3-carboxamide ESI-MS [M+H] (m/z): 721.2.

Example 55

N-(3-fluoro-4-((6-methoxy-7-(3-(pyrrolidin-1-yl)propoxy)quinolin-4-yl)oxy)phenyl)-1-(2-chlorophenyl)-4-oxo-1,4-dihydroquinoline-3-carboxamide ESI-MS [M+H] (m/z): 693.1.

Example 56

N-(3-fluoro-4-((6-methoxy-7-(3-(4-methylpiperazin-1-yl)propoxy)quinolin-4-yl)oxy)phenyl)-1-(2-chlorophenyl)-4-oxo-1,4-dihydroquinoline-3-carboxamide ESI-MS [M+H] (m/z): 722.2.

Example 57

N-(3-fluoro-4-((6-methoxy-7-(3-(4-methylpiperidin-1-yl)propoxy)quinolin-4-yl)oxy)phenyl)-4-oxo-1-(2-(trifluoromethyl)phenyl)-1,4-dihydroquinoline-3-carboxamide ESI-MS [M+H] (m/z): 754.7.

Example 58

N-(3-fluoro-4-((6-methoxy-7-(3-(4-methylpiperidin-1-yl)propoxy)quinolin-4-yl)oxy)phenyl)-1-(3,4-difluorophenyl)-4-oxo-1,4-dihydroquinoline-3-carboxamide ESI-MS [M+H] (m/z): 754.7.

Example 59

N-(3-fluoro-4-((6-methoxy-7-(3-(piperidin-1-yl)propoxy)quinolin-4-yl)oxy)phenyl)-1-(2-(trifluoromethyl)phenyl)-4-oxo-1,4-dihydroquinoline-3-carboxamide ESI-MS [M+H] (m/z): 740.7.

Example 60

N-(3-fluoro-4-((6-methoxy-7-(3-(piperidin-1-yl)propoxy)quinolin-4-yl)oxy)phenyl)-1-(3,4-difluorophenyl)-4-oxo-1,4-dihydroquinoline-3-carboxamide ESI-MS [M+H] (m/z): 708.7.

Example 61

N-(3-fluoro-4-((6-methoxy-7-(3-(piperidin-1-yl)propoxy)cinnolin-4-yl)oxy)phenyl)-1-(2-fluorophenyl)-4-oxo-1,4-dihydrocinnoline-3-carboxamide

Step W 1-(2-amino-4-(3-chloropropoxy)-5-methoxyphenyl)ethanone (Intermediate IX)

To 600 mL of 95% ethylalcohol was added intermediate III (72 g, 0.25 mol) and the mixture was heated to 60° C. Iron powder (112 g, 2 mol) was added to the mixture portion wise. After the completion of addition, the mixture was added drop-wise hydrochloric acid (2 mL) and heated to reflux for 3 h. After the completion of addition, the reaction mixture was filtered without cooling, the filtrate was cooled to room temperature to give precipitate, which was filtered to get off white solid 45 g. Yield: 70%.

Step X 7-(3-chloropropoxy)-6-methoxy-cinnoline-4-one (Intermediate X)

To a mixture of intermediate IX (25.7 g, 0.1 mol) and 200 mL hydrochloric acid (2 mol/L) was added drop-wise 50 mL of the aqueous solution of sodium nitrite (0.2 mol) with the temperature at 0° C. After the completion of addition, the mixture went to room temperature for 4 h, and then heated to 75° C. for 2 h. After the completion of addition, the reaction mixture was cooled, and filtered to give solid which was dissolved in 10% aqueous NaOH (100 mL), adjusted to pH 7 with 2 mol/L HCl aq., The precipitate was filtered to obtain grey solid 23 g. Yield: 85%.

Step Y 6-methoxy-7-(3-(piperidin-1-yl)propoxy)cinnoline-4-one (Intermediate XI)

A mixture of intermediate X (26.8 g, 0.1 mo), acetonitrile (300 mL), piperidino (42 g, 0.5 mol) was heated to reflux for 4 h. After the reaction is complete, the solvent was evaporated in vacuo, the residue was poured into plenty of ether, stirred for 2 h at room temperature. The precipitate was filtered to obtain white solid 30 g. Yield: 94%.

Step Z 4-(2-fluoro-4-nitrophenyl)-6-methoxy-7-(3-(piperidin-1-yl)propoxy)cinnoline (Intermediate XII)

To a solution of intermediate XI (37 g, 0.1 mol) in DMF (350 mL) was added potassium tert-butoxide portionwise at room temperature, the mixture was stirred for 0.5 h, then 3,4-difluoronitrobenzene (17.5 g, 0.11 mol) was added, and the mixture was heated to 90° C. for 2 h. After completion of the reaction, the reaction mixture was filtered without cooling, The filtrate was dissolved in 1000 mL water, to obtain yellow solid 40 g. Yield: 87%.

Step Z-a 3-fluoro-4-((6-methoxy-7-(3-(piperidin-1-yl)propoxy)cinnoline-4-yl)oxy)aniline (M-2)

A stirring solution of intermediate XII (23 g, 0.05 mol) and 95% ethylalcohol (300 mL) was heated to 60° C., then Iron powder (22 g, 0.4 mol) and hydrochloric acid (1 mL) were added portionwise to the reaction mixture, which was heated to reflux for 3 h. After completion of the reaction, the resulting reaction mixture was filtered without cooling. The filtrate was cooled to room temperature to give precipitate, which was filtered to get yellowish white solid 19 g. Yield: 89%.

Step Z-b

N-(3-fluoro-4-((6-methoxy-7-(1-piperidin-1-yl)propoxy)cinnoline-4-yl)oxy)phenyl)-1-(2-fluorophenyl)-4-oxo-1,4-dihydrocinnolinyl-3-carboxamide (Example 61)

To a mixture of intermediate M-2 (0.2 g, 0.48 mmol) and intermediate Q-1 (0.58 mmol) in anhydrous CH2Cl2 was added N,N-diisopropylethylamine (0.07 g, 0.58 mmol), and the reaction mixture was stirred at room temperature for 10 h. After completion of the reaction, the organic layer was washed with 5% aqueous solution of potassium carbonate, brine in sequence, dried with anhydrous magnesium sulfate. The solvent was evaporated in vacuo to obtain target compound N-(3-fluoro-4-((6-methoxy-7-(1-piperidin-1-yl)propoxy)cinnoline-4-yl)oxy)phenyl)-1-(2-fluorophenyl)-4-oxo-1,4-dihydrocinnolinyl-3-carboxamide 0.27 g. Yield: 81%.

ESI-MS [M+H] (m/z): 692.7; $^1$H NMR (300 MHz, DMSO) δ 11.84 (s, 1H), 8.93 (d, J=6.5 Hz, 1H), 8.52 (d, J=7.2 Hz, 1H), 8.33 (dd, J=12.8, 2.1 Hz, 1H), 7.99-7.86 (m, 2H), 7.85-7.78 (m, 3H), 7.78-7.70 (m, 3H), 7.65 (t, J=8.8 Hz, 1H), 7.10 (d, J=8.6 Hz, 1H), 7.02 (d, J=6.4 Hz, 1H), 4.37 (t, J=5.8 Hz, 2H), 4.07 (s, 3H), 3.50 (d, J=11.6 Hz, 4H), 2.92 (d, J=9.6 Hz, 2H), 2.38 (d, J=6.5 Hz, 2H), 1.81 (t, m, 6H).

According to the methods in example 61, substituted M-2 can be synthesized by five steps containing reduction, cyclization reaction with intermediate III as starting material, which then reacts with substituted Q-1 to get compound 62-70.

Example 62

N-(3-fluoro-4-((6-methoxy-7-(3-(4-methylpiperazin-1-yl)propoxy)cinnolin-4-yl)oxy)phenyl)-1-(3-fluorophenyl)-4-oxo-1,4-dihydrocinnoline-3-carboxamide ESI-MS [M+H] (m/z): 707.7; 1H NMR (300 MHz, DMSO) δ 11.77 (s, 1H), 8.95 (d, J=6.5 Hz, 1H), 8.42 (d, J=7.6 Hz, 1H), 8.28-8.09 (m, 2H), 7.98 (t, J=7.1 Hz, 2H), 7.94-7.79 (m, 3H), 7.69 (m, 8.6 Hz, 3H), 7.06 (d, J=8.7 Hz, 1H), 7.02 (d, J=6.4 Hz, 1H), 4.38 (d, J=5.9 Hz, 2H), 4.06 (s, 3H), 3.46 (m, 10H), 2.86 (s, 3H), 2.38 (s, 2H).

Example 63

N-(3-fluoro-4-((6-methoxy-7-(3-(pyrrolidin-1-yl)propoxy)cinnolin-4-yl)oxy)phenyl)-1-(2-fluorophenyl)-4-oxo-1,4-dihydrocinnoline-3-carboxamide ESI-MS [M+H] (m/z): 678.6; $^1$H NMR (300 MHz, DMSO) δ 11.88 (s, 1H), 8.96 (d, J=6.5 Hz, 1H), 8.44 (d, J=7.8 Hz, 1H), 8.28-8.09 (m, 2H), 8.04-7.95 (m, 2H), 7.94-7.83 (m, 2H), 7.80 (s, 1H), 7.77-7.61 (m, 3H), 7.06 (dd, J=10.4, 7.8 Hz, 2H), 4.38 (t, J=5.6 Hz, 2H), 4.05 (d, J=12.1 Hz, 3H), 3.66-3.52 (m, 4H), 3.06 (s, 2H), 2.36 (s, 2H), 1.99 (m, 4H).

Example 64

N-(3-fluoro-4-((6-methoxy-7-(3-(piperidin-1-yl)propoxy)cinnolin-4-yl)oxy)phenyl)-1-(3-fluorophenyl)-4-oxo-1,4-dihydrocinnoline-3-carboxamide ESI-MS [M+H] (m/z): 692.7.

Example 65

N-(3-fluoro-4-((6-methoxy-7-(3-(piperidin-1-yl)propoxy)cinnolin-4-yl)oxy)phenyl)-1-(4-bromophenyl)-4-oxo-1,4-dihydrocinnoline-3-carboxamide ESI-MS [M+H] (m/z): 753.6.

Example 66

N-(3-fluoro-4-((6-methoxy-7-(3-(morpholin-4-yl)propoxy)cinnolin-4-yl)oxy)phenyl)-1-(4-chlorophenyl)-4-oxo-1,4-dihydrocinnoline-3-carboxamide ESI-MS [M+H] (m/z): 711.1.

Example 67

N-(3-fluoro-4-((6-methoxy-7-(3-(4-methylpiperidin-1-yl)propoxy)cinnolin-4-yl)oxy)phenyl)-1-(4-chlorophenyl)-4-oxo-1,4-dihydrocinnoline-3-carboxamide ESI-MS [M+H] (m/z): 723.1.

Example 68

N-(3-fluoro-4-((6-methoxy-7-(3-(morpholin-4-yl)propoxy)cinnolin-4-yl)oxy)phenyl)-1-(4-bromo-2-fluorophenyl)-4-oxo-1,4-dihydrocinnoline-3-carboxamide ESI-MS [M+H] (m/z): 773.5.

Example 69

N-(3-fluoro-4-((6-methoxy-7-(3-(4-methylpiperazin-1-yl)propoxy)cinnolin-4-yl)oxy)phenyl)-1-(4-fluorophenyl)-4-oxo-1,4-dihydrocinnoline-3-carboxamide ESI-MS [M+H] (m/z): 707.7.

Example 70

N-(3-fluoro-4-((6-methoxy-7-(3-(pyrrolidin-1-yl)propoxy)cinnolin-4-yl)oxy)phenyl)-1-(2,4-dichlorophenyl)-4-oxo-1,4-dihydrocinnoline-3-carboxamide ESI-MS [M+H] (m/z): 729.5.

The anti-tumor activity research of the compounds of this invention.

In Vitro Anti-Tumor Cellular Activity.

The in vitro inhibitory activity of the quinoline and cinnoline derivatives described as formula I in this patent was evaluated against the cancer cell lines H460 (human lung cancer cell), HT-29 (colon cancer cell), U87MG (Human malignant glioblastoma cells), MKN-45 (human gastric carcinoma cell), SMMC-7721 (hepatoma cell).

(1) After recovery and passaged 2-3 times stable, the cells were digested with trypsin solution (0.25%) from the bottom of culture bottle. After pouring the cell dissociation buffer to the centrifugetube, nutrient solution was added to stop digestion. The centrifugetube were centrifuged for 10 min under 800 r/min, the liquid supernatant was removed, 5 mL culture solution was added, after mixing by pipetting the cell, took 10 µL cell suspension to the cell counting plat, and adjusted the cell concentration to $10^4$/well. Among the 96 wells, A1 is empty, 100 µL of cell suspension were added to the other wells. The 96 well plates were incubated in the incubator for 24 h.

(2) 50 µL dimethyl sulfoxide was used to dissolve the test samples, and then a suitable amount of culture media was added so as to reach a final concentration of 2 mg/mL. Then the samples were diluted to 20, 4, 0.8, 0.16 0.032 µg/mL in a 24-well plate, respectively.

There were three wells for each concentration, wherein the cell growth in the surrounding two rows and columns was significantly influenced by environments and thus only taken as blank cell wells. The 96-well plates were placed in an incubator and cultivated for 72 hours.

(3) The culture media containing the compounds in the 96-well plates was discarded, and the cells were washed with phosphate buffered solution (PBS) twice. Each well was added with 100 µL MTT (tetrazole) (0.5 mg/mL), and then placed in an incubator to incubate for 4 hours, after which MTT solution was discarded and 100 µL dimethyl sulfoxide was added thereto. The reaction product of survival cells with MTT, i.e. formazan, was dissolved completely by oscillation on a magnetic oscillator, then placed into a microplate reader to measure the results, and the $IC_{50}$ values of compounds could be deduced by Bliss method.

As illustrated in Table 1, all the target compounds showed moderate to excellent antitumour activity against H460, MDA-MB-231, HT-29, MKN-45, U87MG, and SMMC-7721.

TABLE 1

| Example | H460 $IC_{50}$ (µg/mL) | U87MG $IC_{50}$ (µg/mL) | HT-29 $IC_{50}$ (µg/mL) | MKN-45 $IC_{50}$ (µg/mL) | SMMC-7721 $IC_{50}$ (µg/mL) |
|---|---|---|---|---|---|
| Example 1 | 0.04 | 0.18 | 0.18 | 0.27 | 0.57 |
| Example 2 | 0.052 | 0.35 | 0.19 | 0.007 | 0.3 |
| Example 3 | 0.3 | 1.2 | 0.86 | 0.34 | 0.63 |
| Example 4 | 1 | 0.8 | 1.2 | 2 | 0.9 |
| Example 5 | 0.77 | 1.2 | 0.42 | 0.2 | 0.25 |
| Example 6 | 1.7 | 1.4 | 0.63 | 0.1 | 1.3 |
| Example 7 | 1.7 | 1.5 | 0.82 | 1.4 | 0.63 |

TABLE 1-continued

| Example | H460 IC$_{50}$ (µg/mL) | U87MG IC$_{50}$ (µg/mL) | HT-29 IC$_{50}$ (µg/mL) | MKN-45 IC$_{50}$ (µg/mL) | SMMC-7721 IC$_{50}$ (µg/mL) |
|---|---|---|---|---|---|
| Example 8 | 0.45 | — | 0.78 | 0.25 | 0.41 |
| Example 9 | 0.007 | 1.2 | 0.17 | 0.0075 | 0.65 |
| Example 10 | 0.06 | 0.86 | 0.42 | 0.087 | 1 |
| Example 11 | 0.06 | 3.5 | 0.38 | 0.12 | 0.63 |
| Example 12 | 0.91 | 0.55 | 0.41 | 1.2 | 0.67 |
| Example 13 | 0.081 | 0.45 | 0.18 | 0.23 | 0.67 |
| Example 14 | 0.47 | 0.15 | 0.31 | 0.45 | 1.1 |
| Example 15 | 1 | 0.2 | 0.6 | 0.8 | 1.5 |
| Example 16 | 0.69 | 0.2 | 0.57 | 1.1 | 0.45 |
| Example 17 | 1.4 | 0.9 | 1.8 | 2.1 | 0.5 |
| Example 18 | 1.3 | 0.8 | 0.9 | 1.5 | 2.1 |
| Example 19 | 2.2 | 1.2 | 0.54 | 0.86 | 1.6 |
| Example 20 | 1.1 | 1.3 | 0.7 | 1.6 | 0.5 |
| Example 21 | 0.8 | 0.7 | 0.8 | 0.6 | 1.4 |
| Example 22 | 0.54 | 0.96 | 0.81 | 0.28 | 0.54 |
| Example 23 | 1 | 1.3 | 0.7 | 0.9 | 1.4 |
| Example 24 | 1.1 | 2.8 | 1.4 | 0.8 | 0.86 |
| Example 25 | 0.89 | 2.9 | 1.1 | 1.5 | 0.76 |
| Example 26 | 0.8 | 1.8 | 1.4 | 0.7 | 1.6 |
| Example 27 | 1.5 | 0.6 | 1.8 | 2.1 | 0.9 |
| Example 28 | 2.3 | 1.6 | 0.9 | 1.8 | 1.3 |
| Example 29 | 0.77 | 0.74 | 0.44 | 0.67 | 1.2 |
| Example 30 | 0.7 | 0.27 | 0.49 | 0.5 | 0.1 |
| Example 31 | 0.77 | 0.26 | 0.27 | 0.18 | 0.33 |
| Example 32 | 0.7 | 0.65 | 0.77 | 1.2 | 0.66 |
| Example 33 | 2.2 | 1.4 | 0.9 | 1.1 | 1.6 |
| Example 34 | 0.7 | 0.65 | 0.43 | 1.3 | 1.5 |
| Example 35 | 2.5 | 1.3 | 0.9 | 2.1 | 1.5 |
| Example 36 | 1.1 | 1.5 | 0.7 | 1.3 | 0.87 |
| Example 37 | 1.9 | 2.1 | 0.9 | 2.3 | 1.5 |
| Example 38 | 1.6 | 1.1 | 1.8 | 2.1 | 0.98 |
| Example 39 | 2.3 | 1.8 | 0.87 | 1.4 | 2.1 |
| Example 42 | 2.7 | 2.1 | 1.5 | — | 1.6 |
| Example 43 | 0.53 | 0.77 | 1.2 | 0.45 | 1.8 |
| Example 44 | 1.6 | 0.84 | 1.2 | 1.8 | 2.1 |
| Example 45 | 1 | 2.1 | 0.87 | 1.6 | 2.3 |
| Example 46 | 0.98 | 0.72 | 1.5 | 0.67 | 1.3 |
| Example 47 | 0.54 | 0.49 | 0.57 | 0.34 | 1.1 |
| Example 48 | 0.7 | 0.88 | 0.65 | 1.1 | 0.56 |
| Example 49 | 1.1 | 0.9 | 1.3 | 0.76 | 0.99 |
| Example 50 | 0.58 | 0.35 | 0.38 | 0.45 | 0.87 |
| Example 51 | 0.58 | 0.28 | 0.41 | 0.24 | 0.53 |
| Example 52 | 1.4 | 0.87 | 1.1 | 0.67 | 1.8 |
| Example 53 | 0.79 | 0.21 | 0.93 | 0.47 | 0.29 |
| Example 54 | 0.63 | 0.14 | 0.63 | 0.49 | 0.52 |
| Example 55 | 0.74 | 0.18 | 0.37 | 0.29 | 0.53 |
| Example 56 | 0.75 | 0.12 | 0.2 | 0.21 | 0.74 |
| Example 57 | 1.3 | 1.1 | 0.87 | 0.91 | 0.58 |
| Example 58 | 1.4 | 2.1 | 0.95 | 1.8 | 1.1 |
| Example 62 | 0.8 | 1.4 | 2.1 | 3.6 | 2.1 |
| Example 63 | 1.6 | 1.8 | 1.3 | — | 0.9 |
| Example 64 | 1.8 | 2.7 | 3.2 | 3.3 | 1.9 |
| Example 66 | 0.89 | 2.1 | 1.4 | 2.4 | 1.7 |
| Example 67 | 2.5 | 1.7 | 0.96 | 2.2 | 1.6 |
| Example 68 | 1.5 | 1.3 | 2.1 | 2.5 | 2.9 |
| Example 69 | 2.3 | 1.8 | 2.1 | 2.6 | 1.3 |
| Example 70 | 2.6 | 2.1 | 3.2 | — | 1.8 |
| Cisplatin | 0.23 | 0.19 | 1 | 0.68 | 0.9 | c-Met Kinase Assay:

c-Met kinase activity was measured with an ELISA reader. To the plate filled with 0.25 mg/mL PGT, the compounds, 50 pM c-Met (His-tagged recombinant human Met (Amino acids 974-ends), by baculovirus expression) and 5 µM ATP in buffer solution (25 mM MOPS, pH 7.4, 5 mM MgCl2, 0.5 raM MnCl$_2$, 100 µM sodium orthovanadate, 0.01% Triton X-100, 1 mM DTT, 1% of DMSO1% (v/v)) was added, the solution was incubated for 20 min. The reaction mixture was removed by washing with 0.2 µg/mL conjugated horseradish peroxidase (HRP) monoclonal antibody specific for phosphotyrosine (PY20) detecting phosphorylation of the substrate polymer. 1M phosphoric acid was added to terminate the color, the chromogenic substrate (TMB) was tested by spectrophotometry at 450 nm. The c-Met kinase inhibition data was illustrated in Table 2.

TABLE 2

| Example | c-Met IC$_{50}$ (µg/mL) |
|---|---|
| Example 1 | 0.05 |
| Example 2 | 0.03 |
| Example 3 | 0.2 |
| Example 4 | 0.6 |
| Example 5 | 0.4 |
| Example 6 | 0.8 |
| Example 7 | 0.5 |
| Example 9 | 0.3 |
| Example 10 | 0.01 |
| Example 11 | 0.03 |
| Example 12 | 0.1 |
| Example 13 | 1.1 |
| Example 14 | 0.05 |
| Example 15 | 0.66 |
| Example 16 | 0.9 |
| Example 17 | 0.2 |
| Example 18 | 0.5 |
| Example 19 | 1.2 |
| Example 20 | 1.5 |
| Example 21 | 0.9 |
| Example 22 | 1.1 |
| Example 23 | 0.32 |
| Example 24 | 0.9 |
| Example 26 | 0.3 |
| Example 27 | 0.4 |
| Example 28 | 1.3 |
| Example 29 | 1.1 |
| Example 31 | 0.2 |
| Example 32 | 0.1 |
| Example 33 | 1.1 |
| Example 35 | 1.1 |
| Example 36 | 0.67 |
| Example 37 | 0.69 |
| Example 38 | 1.1 |
| Example 39 | 1.0 |
| Example 40 | 0.9 |
| Example 41 | 1.4 |
| Example 42 | 1.0 |
| Example 43 | 0.7 |
| Example 44 | 1.1 |
| Example 46 | 0.8 |
| Example 47 | 0.4 |
| Example 48 | 1.1 |
| Example 49 | 0.6 |
| Example 50 | 0.6 |
| Example 51 | 0.2 |
| Example 52 | 1.6 |
| Example 53 | 0.5 |
| Example 54 | 0.7 |
| Example 55 | 0.9 |
| Example 56 | 0.1 |
| Example 57 | 0.8 |
| Example 58 | 0.72 |
| Example 60 | 0.29 |
| Example 63 | 0.8 |
| Example 65 | 0.68 |
| Example 66 | 0.4 |
| Example 67 | 1.1 |
| Example 68 | 0.9 |
| Example 69 | 1.1 |
| Example 70 | 0.7 |

It can be clearly seen from the above test results, the protected compounds in formula I in this invention, have good anti-tumor activity in vitro, and are better than the anticancer drug cisplatin.

Compounds of Formula I in the invention may be used alone, but usually given with a pharmaceutically acceptable carrier, which is selected according to the desired route of administration and standard pharmaceutical practice, the following preparation methods of such various pharmaceutical dosages (tablets, capsules, injections, aerosols, suppositories, films, pills, liniment, topical ointments) were used to describe new application in the pharmaceutical field.

Example 71

Tablet 10 g compound (e.g., the compound of Example 12) containing the compound of claim 1 was mixed homogeneously with 20 g adjuvants and tabletted into 100 tablets by general compression method, 300 mg each tablet.

Example 72

Capsule 10 g compound (e.g., the compound of Example 36) containing the compound of claim 1 was mixed homogeneously with 20 g adjuvants according to the requirements of pharmaceutical capsules, and filled into empty capsules, 300 mg each capsule.

Example 73

Injection 10 g compound (e.g., the compound of Example 1) containing the compound of claim 1 was absorbed by activative charcoal by conventional pharmaceutical method, filtered through 0.65 μm microporous membrane and filled into nitrogen bottle to prepare water injection preparation, 2 mL each bottle, and 100 bottles in total.

Example 74

Aerosol 10 g compound (e.g., the compound of Example 22) containing the compound of claim 1 was dissolved with a suitable amount of propylene glycol, and added with distilled water and other adjuvants to get 500 mL clear solution.

Example 75

Suppository 10 g compound (e.g., the compound of Example 19) containing the compound of claim 1 was grinded and a suitable amount of glycerol was added and mixed homogeneously. Then melt glycerol gelatin was added and grinded homogeneously, and the mixture was poured into a mold coated with lubricant to produce 50 suppository particles.

Example 76

Film 10 g compound (e.g., the compound of Example 13) containing the compound of claim 1 was mixed and expanded with polyvinyl alcohol, pharmaceutically acceptable glycerol, water etc., and dissolved by heating. After filtration on an 80 mesh screen, the compound of Example 18 was added to the filtrate and dissolved therein by agitation. 100 films were produced by coater machine.

Example 77

Dripping Pill 10 g compound (e.g., the compound of Example 17) containing the compound of claim 1 was mixed homogeneously with 50 g substrate such as gelatin by heating and melting, then the mixture was dropped into a liquid paraffin at low temperature. 1000 pills of dripping pill were produced.

Example 78

Liniment for External Use 10 g compound (e.g., the compound of Example 31) containing the compound of claim 1 was mixed and ground with 2.5 g adjuvants such as emulsifier by conventional formulation methods, then 200 mL water was added to prepare the liniment for external use.

Example 79

Ointment 10 g compound (e.g., the compound of Example 47) containing the compound of claim 1 was ground and then mixed homogeneously with 500 g oleaginous base such as Vaseline.

Although the present invention has been described through specific embodiments, but modifications and equivalent changes to those skilled person in this field are apparent, and they are included within the scope of the invention.

What is claimed is:

1. A compound of formula I or a pharmaceutically acceptable salt, hydrate, solvate or prodrug thereof,

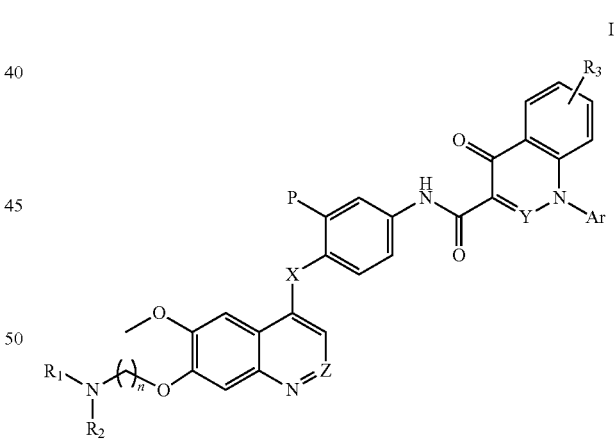

wherein:
P is F or H;
X is O, S, NH or NCH$_3$;
Z is N or CH;
Y is N or CH;
n is an integer between 1 and 6;
$R_1$ and $R_2$, which are same or different, are selected independently from the group consisting of H, ($C_1$-$C_{10}$) alkyl, ($C_3$-$C_7$) cycloalkyl, ($C_2$-$C_{10}$)alkenyl and ($C_2$-$C_{10}$) alkynyl, wherein said alkyl, cycloalkyl, alkenyl and alkynyl are optionally substituted with 1 to 3 same or different $R_4$;

or $R_1$ and $R_2$ are covalently bonded together with the nitrogen to which they are attached to form 5- to 10-membered heterocyclic radical or 5- to 10-membered heteroaryl radical, said heterocyclic radical or heteroaryl radical may have optionally 1 to 4 heteroatoms selected from N, O, and S except the nitrogen atom to which $R_1$ and $R_2$ are attached, said heterocyclic radical may optionally have 1 to 2 carbon-carbon double bond or triple bond, said heterocyclic and heteroaryl radicals can be optionally substituted with 1 to 3 same or different $R_4$;

$R_4$ is $(C_1-C_4)$ alkyl, $(C_1-C_4)$alkoxyl, halogen, hydroxyl, cyano, carboxyl, or an ester group;

$R_3$ is hydrogen or 1 to 3 substituents selected independently from the group consisting of hydroxyl,
halogen,
nitro,
amino,
cyano,
$(C_1-C_6)$ alkyl,
$(C_2-C_6)$ alkenyl,
$(C_2-C_6)$ alkynyl,
$(C_1-C_6)$ alkoxyl,
$(C_1-C_6)$ alkylsulfanyl, $(C_1-C_6)$ alkyl or $(C_1-C_6)$ alkoxyl or $(C_1-C_6)$ alkylsulfanyl substituted optionally with hydroxyl, amino or halogen,
amino substituted with 1 or 2 $(C_1-C_6)$ alkyl,
$(C_1-C_6)$alkylamido, carboxy group which can be free, salts, or form ester group,
$(C_1-C_6)$ alkylsulfinyl,
sulfonyl, $(C_1-C_6)$alkylacyl,
aminoformyl,
aminoformyl substituted with 1 or 2 $(C_1-C_6)$alkyl, and
$(C_1-C_3)$alkylenedioxo;

Ar represents $(C_6-C_{10})$ aryl, or 5- to 10-membered heteroaryl radical, wherein said heteroaryl radical may have 1 to 3 heteroatom(s) selected from N, O, and S, and Ar can be optionally substituted with 1 to 3 same or different $R_5$;

$R_5$ is hydroxyl,
halogen,
nitro,
amino,
cyano,
$(C_1-C_6)$ alkyl,
$(C_2-C_6)$ alkenyl,
$(C_2-C_6)$ alkynyl,
$(C_1-C_6)$ alkoxyl,
$(C_1-C_6)$ alkyl or $(C_1-C_6)$ alkoxyl optionally substituted with hydroxyl, amino or halogen, amino substituted with 1 or 2 $(C_1-C_6)$ alkyl,
carboxy group which can be free, salts, or form ester group,
$(C_1-C_6)$ alkylsulfinyl,
sulfonyl,
$(C_1-C_6)$ alkoxyl $(C_1-C_6)$ alkyl,
$(C_1-C_6)$alkylacyl,
aminoformyl,
aminoformyl substituted optionally with 1 or 2 $(C_1-C_6)$ alkyl, or
$(C_1-C_3)$alkylenedioxo.

2. The compound of formula I, or a pharmaceutically acceptable salt, hydrate, solvate or prodrug thereof according to claim 1, Wherein, P is F;
X is O or NH;
n is an integer between 1 and 4;

$R_1$ and $R_2$, which are the same or different, are selected independently from the group consisting of H, $(C_1-C_6)$ alkyl, $(C_3-C_6)$cycloalkyl, $(C_2-C_6)$ alkenyl and $(C_2-C_6)$ alkynyl, wherein said alkyl, cycloalkyl, alkenyl and alkynyl are optionally substituted with 1 to 3 same or different $R_4$;

or $R_1$ and $R_2$ are covalently bonded together with the nitrogen to which they are attached to form 5- to 10-membered heterocyclic radical, said heterocyclic radical may have optionally 1 to 4 heteroatoms selected from N, O, and S except the nitrogen atom to which $R_1$ and $R_2$ are attached, said heterocyclic radical may optionally have 1 to 2 carbon-carbon double bond or triple bond, said heterocyclic radical can be optionally substituted with 1 to 3 same or different $R_4$;

$R_4$ is $(C_1-C_4)$ alkyl, $(C_1-C_4)$alkoxyl, halogen, hydroxyl, cyano, carboxyl, or an ester group;

Ar represents phenyl, naphthyl, or 5- to 10-membered heteroaryl radical, wherein said heteroaryl radical may have 1 to 3 heteroatom(s) selected from N, O, and S, and Ar can be optionally substituted with 1 to 3 same or different $R_5$.

3. The compound of formula I, or a pharmaceutically acceptable salt, hydrate, solvate or prodrug thereof according to claim 2, wherein:

X is O;

$R_1$ and $R_2$, which are the same or different, are selected independently from the group consisting of $(C_1-C_6)$ alkyl, and $(C_3-C_6)$cycloalkyl, wherein said alkyl, cycloalkyl are optionally substituted with 1 to 3 same or different $R_4$;

or $R_1$ and $R_2$ are covalently bonded together with the nitrogen to which they are attached to form 5- to 6-membered heterocyclic radical, said heterocyclic radical may have optionally 1 to 4 heteroatoms selected from N, O, and S except the nitrogen atom to which $R_1$ and $R_2$ are attached, said heterocyclic radical may optionally have 1 to 2 carbon-carbon double bond or triple bond, said heterocyclic radical can be optionally substituted with 1 to 3 same or different $R_4$.

4. The compound of formula I, or a pharmaceutically acceptable salt, hydrate, solvate or prodrug thereof according to claim 3, wherein:

$R_1$ and $R_2$ are covalently bonded together with the nitrogen to which they are attached to form 5- to 6-membered saturated heterocyclic radical, said saturated heterocyclic radical may have optionally 1 to 4 heteroatoms selected from N, O, and S except the nitrogen atom to which $R_1$ and $R_2$ are attached, said saturated heterocyclic radical can be optionally substituted with 1 to 3 same or different $R_4$;

$R_4$ is $(C_1-C_4)$alkyl;

$R_3$ is hydrogen or 1 to 3 substituent(s) optionally selected from halogen, $(C_1-C_4)$ alkyl, $(C_1-C_4)$ alkoxyl, trifluoromethyl, and trifluoromethoxy;

Ar represents phenyl, naphthyl, quinolyl, pyridyl, furyl, thienyl or pyrrolyl, wherein Ar can be optionally substituted with 1 to 3 same or different $R_5$;

$R_5$ is halogen,
$(C_1-C_4)$ alkyl,
$(C_1-C_4)$ alkoxyl,
$(C_1-C_4)$ alkyl or $(C_1-C_4)$ alkoxyl optionally substituted with halogen, amino substituted with 1 or 2 $(C_1-C_6)$ alkyl,
$(C_1-C_4)$ alkoxyl$(C_1-C_4)$ alkyl,
$(C_1-C_6)$alkylacyl,
aminoformyl, aminoformyl substituted with 1 or 2 ($C_1$-$C_6$) alkyl, or ($C_1$-$C_3$)alkylenedioxo.

5. The compound of formula I, or a pharmaceutically acceptable salt, hydrate, solvate or prodrug thereof according to claim 4, wherein:
$R_1$ and $R_2$ are covalently bonded together with the nitrogen to which they are attached to form 1-piperidino, 4-morpholino, 4-methyl-1-piperazinyl, 1-piperazinyl, 4-methyl-1-piperidino, 1-pyrrolidinyl, or 4-sulfomorpholino;
Ar represents phenyl or phenyl optionally substituted with 1 to 3 same or different $R_5$.

6. The compound of general formula I, or a pharmaceutically acceptable salt, hydrate, solvate or prodrug thereof according to claim 5, wherein,
Z is N.

7. The compound of formula I, or a pharmaceutically acceptable salt, hydrate, solvate or prodrug thereof according to claim 5, wherein:
Z is CH.

8. The compound of formula I, or a pharmaceutically acceptable salt, hydrate, solvate or prodrug thereof according to claim 7, wherein:
Y is CH.

9. The compound of formula I, or a pharmaceutically acceptable salt, hydrate, solvate or prodrug thereof according to claim 7, wherein:
Y is N.

10. The compound of formula I, or a pharmaceutically acceptable salt, hydrate, solvate or prodrug thereof according to claim 9, wherein:
$R_1$ and $R_2$ are covalently bonded together with the nitrogen to which they are attached to form 1-piperidino, 4-morpholino, 4-methyl-1-piperazinyl, 4-methyl-1-piperidino, or 1-pyrrolidinyl;
n is 3;
$R_3$ is hydrogen;
Ar represents phenyl or phenyl optionally substituted with 1 to 3 same or different $R_5$;
$R_5$ is halogen, ($C_1$-$C_4$) alkyl, ($C_1$-$C_4$) alkoxyl, trifluoromethyl or trifluoromethoxy.

11. The compound of formula I, or a pharmaceutically acceptable salt, hydrate, solvate or prodrug thereof according to claim 10, wherein:
$R_5$ is F, Cl or trifluoromethyl.

12. The compound of formula I, or a pharmaceutically acceptable salt, hydrate, solvate or prodrug thereof according to claim 1, wherein the compound of general formula I is selected from the following compounds:
N-(3-fluoro-4-((6-methoxy-7-(3-(pyrrolidin-1-yl)propoxy)quinolin-4-yl)oxy)phenyl)-1-(2-(trifluoromethyl)phenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(2-chlorophenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(4-bromophenyl)-4-oxo-1,4-dihydrocinnoline-3-carboxamide;
N-(3-fluoro-4-((6-methoxy-7-(3-(morpholin-4-ylpropoxy)quinolin-4-yl)oxy)phenyl)-1-(2-(trifluoromethyl)phenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(2-(trifluoromethyl)phenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(3-(trifluoromethyl)phenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(2-fluorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2-(trifluoromethyl)phenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(3-fluorophenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(4-chlorophenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(3,4-difluorophenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(3,4-difluorophenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(4-fluorophenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(2-fluorophenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(2-chlorophenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(2-chlorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2-chlorophenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(2-bromo-4-fluorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2-bromo-4-fluorophenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(2-chloro-5-(trifluoromethyl)phenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(2-chloro-5-(trifluoromethyl)phenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(2-chloro-5-(trifluoromethyl)phenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2-chloro-5-(trifluoromethyl)phenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(2,4-dimethylphenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(2,4-dimethylphenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2,4-dimethylphenyl)-4-oxo-1,4-dihydrocinnoline-3-carboxamide;

N-(3-fluoro-4-((6-methoxy-7-(3-(piperidin-1-yl)propoxy)quinolin-4-yl)oxy)phenyl)-1-(2,4-dichlorophenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(2,4-dichlorophenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(2,6-dichlorophenyl)-4-oxo-1,4-dihydrocinnoline-3-carboxamide;
N-(3-fluoro-4-((6-methoxy-7-(3-(4-methylpiperidin-1-yl)propoxy)quinolin-4-yl)oxy)phenyl)-1-(2,6-dichlorophenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(2,6-dichlorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2,6-dichlorophenyl)-4-oxo-1,4-dihydrocinnoline-3-carboxamide;
N-(3-fluoro-4-((6-methoxy-7-(3-(morpholin-4-yl)propoxy)quinolin-4-yl)oxy)phenyl)-1-(2-chlorophenyl)-4-oxo-1,4-dihydrocinnoline-3-carboxamide;
N-(3-fluoro-4-((6-methoxy-7-(3-(morpholin-4-yl)propoxy)quinolin-4-yl)oxy)phenyl)-1-(2-bromophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2-bromophenyl)-4-oxo-1,4-dihydrocinnoline-3-carboxamide;
N-(3-fluoro-4-((6-methoxy-7-(3-(morpholin-4-yl)propoxy)quinolin-4-yl)oxy)phenyl)-1-(4-fluorophenyl)-4-oxo-1,4-dihydrocinnoline-3-carboxamide;
N-(3-fluoro-4-((6-methoxy-7-(3-(morpholin-4-yl)propoxy)quinolin-4-yl)oxy)phenyl)-1-(2-(trifluoromethoxy)phenyl)-4-oxo-1,4-dihydrocinnoline-3-carboxamide;
N-(3-fluoro-4-((6-methoxy-7-(3-(piperidin-1-yl)propoxy)quinolin-4-yl)oxy)phenyl)-1-(2-(trifluoromethoxy)phenyl)-4-oxo-1,4-dihydrocinnoline-3-carboxamide;
N-(3-fluoro-4-((6-methoxy-7-(3-(morpholin-4-yl)propoxy)quinolin-4-yl)oxy)phenyl)-1-(4-bromophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(4-bromophenyl)-4-oxo-1,4-dihydrocinnoline-3-carboxamide;
N-(3-fluoro-4-((6-methoxy-7-(3-(pyrrolidin-1-yl)propoxy)quinolin-4-yl)oxy)phenyl)-1-(2-fluorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(4-fluorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2,4-dichlorophenyl)-4-oxo-1,4-dihydrocinnoline-3-carboxamide;
N-(3-fluoro-4-((6-methoxy-7-(3-(4-methylpiperazin-1-yl)propoxy)quinolin-4-yl)oxy)phenyl)-1-(2-(trifluoromethyl)phenyl)-4-oxo-1,4-dihydrocinnoline-3-carboxamide;
N-(3-fluoro-4-((6-methoxy-7-(3-(morpholin-4-yl)propoxy)quinolin-4-yl)oxy)phenyl)-1-(2-fluorophenyl)-4-oxo-1,4-dihydrocinnoline-3-carboxamide.

13. The compound of formula I, or a pharmaceutically acceptable salt, hydrate, solvate or prodrug thereof according to claim 1, selected from the following compounds:
N-(3-fluoro-4-((6-methoxy-7-(3-(4-methylpiperazin-1-yl)propoxy)quinolin-4-yl)oxy)phenyl)-1-(4-fluorophenyl)-4-oxo-1,4-dihydroquinoline-3-carboxamide;
N-(3-fluoro-4-((6-methoxy-7-(3-(4-methylpiperidin-1-yl)propoxy)quinolin-4-yl)oxy)phenyl)-1-(2-fluorophenyl)-4-oxo-1,4-dihydroquinoline-3-carboxamide;
N-(3-fluoro-4-((6-methoxy-7-(3-(morpholin-4-yl)propoxy)quinolin-4-yl)oxy)phenyl)-4-oxo-1-(2-(trifluoromethyl)phenyl)-1,4-dihydroquinoline-3-carboxamide;
N-(3-fluoro-4-((6-methoxy-7-(3-(piperidin-1-yl)propoxy)quinolin-4-yl)oxy)phenyl)-1-(4-fluorophenyl)-4-oxo-1,4-dihydroquinoline-3-carboxamide;
N-(3-fluoro-4-((6-methoxy-7-(3-(piperidin-1-yl)propoxy)quinolin-4-yl)oxy)phenyl)-1-(2-fluorophenyl)-4-oxo-1,4-dihydroquinoline-3-carboxamide;
N-(3-fluoro-4-((6-methoxy-7-(3-(pyrrolidin-1-yl)propoxy)quinolin-4-yl)oxy)phenyl)-1-(2-fluorophenyl)-4-oxo-1,4-dihydroquinoline-3-carboxamide;
N-(3-fluoro-4-((6-methoxy-7-(3-(4-methylpiperazin-1-yl)propoxy)quinolin-4-yl)oxy)phenyl)-1-(2-fluorophenyl)-4-oxo-1,4-dihydroquinoline-3-carboxamide;
N-(3-fluoro-4-((6-methoxy-7-(3-(piperidin-1-yl)propoxy)quinolin-4-yl)oxy)phenyl)-1-(2-chlorophenyl)-4-oxo-1,4-dihydroquinoline-3-carboxamide;
N-(3-fluoro-4-((6-methoxy-7-(3-(4-methylpiperidin-1-yl)propoxy)quinolin-4-yl)oxy)phenyl)-1-(2-chlorophenyl)-4-oxo-1,4-dihydroquinoline-3-carboxamide;
N-(3-fluoro-4-((6-methoxy-7-(3-(pyrrolidin-1-yl)propoxy)quinolin-4-yl)oxy)phenyl)-1-(2-chlorophenyl)-4-oxo-1,4-dihydroquinoline-3-carboxamide;
N-(3-fluoro-4-((6-methoxy-7-(3-(4-methylpiperazin-1-yl)propoxy)quinolin-4-yl)oxy)phenyl)-1-(2-chlorophenyl)-4-oxo-1,4-dihydroquinoline-3-carboxamide;
N-(3-fluoro-4-((6-methoxy-7-(3-(4-methylpiperidin-1-yl)propoxy)quinolin-4-yl)oxy)phenyl)-4-oxo-1-(2-(trifluoromethyl)phenyl)-1,4-dihydroquinoline-3-carboxamide;
N-(3-fluoro-4-((6-methoxy-7-(3-(4-methylpiperidin-1-yl)propoxy)quinolin-4-yl)oxy)phenyl)-1-(3,4-difluorophenyl)-4-oxo-1,4-dihydroquinoline-3-carboxamide;
N-(3-fluoro-4-((6-methoxy-7-(3-(piperidin-1-yl)propoxy)quinolin-4-yl)oxy)phenyl)-1-(3,4-difluorophenyl)-4-oxo-1,4-dihydroquinoline-3-carboxamide.

14. The compound of general formula I, or a pharmaceutically acceptable salt, hydrate, solvate or prodrug thereof according to claim 1, wherein the compound of general formula I is selected from the following compounds:
N-(3-fluoro-4-((6-methoxy-7-(3-(piperidin-1-yl)propoxy)cinnolin-4-yl)oxy)phenyl)-1-(2-fluorophenyl)-4-oxo-1,4-dihydrocinnoline-3-carboxamide;
N-(3-fluoro-4-((6-methoxy-7-(3-(4-methylpiperazin-1-yl)propoxy)cinnolin-4-yl)oxy)phenyl)-1-(3-fluorophenyl)-4-oxo-1,4-dihydrocinnoline-3-carboxamide;
N-(3-fluoro-4-((6-methoxy-7-(3-(pyrrolidin-1-yl)propoxy)cinnolin-4-yl)oxy)phenyl)-1-(2-fluorophenyl)-4-oxo-1,4-dihydrocinnoline-3-carboxamide;
N-(3-fluoro-4-((6-methoxy-7-(3-(piperidin-1-yl)propoxy)cinnolin-4-yl)oxy)phenyl)-1-(3-fluorophenyl)-4-oxo-1,4-dihydrocinnoline-3-carboxamide;
N-(3-fluoro-4-((6-methoxy-7-(3-(piperidin-1-yl)propoxy)cinnolin-4-yl)oxy)phenyl)-1-(4-bromophenyl)-4-oxo-1,4-dihydrocinnoline-3-carboxamide;
N-(3-fluoro-4-((6-methoxy-7-(3-(morpholin-4-yl)propoxy)cinnolin-4-yl)oxy)phenyl)-1-(4-chlorophenyl)-4-oxo-1,4-dihydrocinnoline-3-carboxamide;
N-(3-fluoro-4-((6-methoxy-7-(3-(4-methylpiperidin-1-yl)propoxy)cinnolin-4-yl)oxy)phenyl)-1-(4-chlorophenyl)-4-oxo-1,4-dihydrocinnoline-3-carboxamide;

N-(3-fluoro-4-((6-methoxy-7-(3-(morpholin-4-yl)propoxy)cinnolin-4-yl)oxy)phenyl)-1-(4-bromo-2-fluorophenyl)-4-oxo-1,4-dihydrocinnoline-3-carboxamide;

N-(3-fluoro-4-((6-methoxy-7-(3-(4-methylpiperazin-1-yl)propoxy)cinnolin-4-yl)oxy)phenyl)-1-(4-fluorophenyl)-4-oxo-1,4-dihydrocinnoline-3-carboxamide;

N-(3-fluoro-4-((6-methoxy-7-(3-(pyrrolidin-1-yl)propoxy)cinnolin-4-yl)oxy)phenyl)-1-(2,4-dichlorophenyl)-4-oxo-1,4-dihydrocinnoline-3-carboxamide.

15. A pharmaceutical composition, comprising the compound or pharmaceutically acceptable salt and/or hydrate, solvate, or prodrug thereof according to claim 1 as active ingredient and pharmaceutically acceptable excipient.

16. A method for treating a proliferative disease in a patient, comprising administering to the patient the compound of claim 1, wherein said proliferative disease is psoriasis, benign prostatic hypertrophy, atherosclerosis, or restenosis.

17. A method for treating cancer in a patient, comprising administering to the patient the compound of claim 1, wherein said cancer is lung cancer, liver cancer, gastric cancer, colon cancer, or breast cancer.

\* \* \* \* \*